US008835395B2

(12) United States Patent
Sun et al.

(10) Patent No.: US 8,835,395 B2
(45) Date of Patent: Sep. 16, 2014

(54) PROTEIN PEPTIDE HYDROGELS

(75) Inventors: Xiuzhi Susan Sun, Manhattan, KS (US);
Hongzhou Huang, Manhattan, KS (US)

(73) Assignee: Kansas State University Research Foundation, Manhattan, KS (US)

( * ) Notice: Subject to any disclaimer, the term of this patent is extended or adjusted under 35 U.S.C. 154(b) by 0 days.

(21) Appl. No.: 13/583,528

(22) PCT Filed: Mar. 10, 2011

(86) PCT No.: PCT/US2011/027972
§ 371 (c)(1),
(2), (4) Date: Sep. 7, 2012

(87) PCT Pub. No.: WO2011/112856
PCT Pub. Date: Sep. 15, 2011

(65) Prior Publication Data
US 2013/0018004 A1 Jan. 17, 2013

Related U.S. Application Data

(60) Provisional application No. 61/312,323, filed on Mar. 10, 2010.

(51) Int. Cl.
| A61K 38/10 | (2006.01) |
| C07K 7/08 | (2006.01) |
| C07K 14/00 | (2006.01) |
| A61L 27/22 | (2006.01) |
| A61K 51/12 | (2006.01) |
| A61L 27/52 | (2006.01) |
| C07K 7/00 | (2006.01) |

(52) U.S. Cl.
CPC ............... *C07K 14/00* (2013.01); *A61L 27/22* (2013.01); *A61K 51/1213* (2013.01); *A61K 38/10* (2013.01); *A61L 27/52* (2013.01); *C07K 7/00* (2013.01)
USPC .......................................... 514/21.4; 530/326

(58) Field of Classification Search
CPC .................... A61K 2039/55516; A61K 39/12; A61K 39/145; A61K 39/39; A61K 38/10; A61K 51/1213; C07K 7/00
USPC ........... 424/204.1, 234.1, 184.1, 277.1, 278.1
See application file for complete search history.

(56) References Cited

U.S. PATENT DOCUMENTS

| 7,008,635 B1 | 3/2006 | Coury et al. |
| 2002/0151650 A1 | 10/2002 | Pathak et al. |
| 2004/0171545 A1 | 9/2004 | Chaikof et al. |

FOREIGN PATENT DOCUMENTS

| WO | 0117574 | 3/2001 |
| WO | WO 2006127048 A2 * | 11/2006 |

OTHER PUBLICATIONS

Monica C. Branco, Macromolecular diffusion and release from self-assembled B-hairpin peptide hydrogels, 2009, Biomaterials, 30(7):1339-1347.*
Rudinger, Peptide Hormones, JA Parsons, Ed., 1976, pp. 1-7.*
SIGMA, 2004, pp. 1-2.*
Berendsen, A Glimpae of the Holy Grail?, Science, 1998, 282, pp. 642-643.*
Voet et al, Biochemistry, John Wiley & Sons Inc., 1995, pp. 235-241.*
Ngo et al, Computational Complexity, Protein Structure Protection, and the Levinthal Paradox, 1994, pp. 491-494.*
Bradley et al., Limits of Cooperativity in a Structurally Modular Protein: Response of the Notch Ankyrin Domain to Analogous Alanine Substitutions in Each Repeat, J. Mol. BIoL (2002) 324, 373-386.*
Oscar D. Monera, Relationship of Sidechain Hydrophobicity and alpha-Helical Propensity on the Stability of the single stranded Amphipathic alpha-helix, 1995, Journal of Peptide Science, vol. 1, pp. 319-329.*
Rapaport, Hanna "Hydrogel Scaffolds of Amphiphilic and Acidic Beta-Sheet Peptides," Advance Functional Materials, Sep. 22, 2008, 2889-2896, vol. 18, Published online Sep. 22, 2008.
Petra, Wendy A., "Reversible Hydrogels from Self-Assembling Artificial Proteins," www.sciencemag.org, Jul. 17, 1998, vol. 281.
Teesch, Lynn M., "Intrinsic Interactions between Alkaline-Earth Metal Ions and Peptides: A Gas-Phase Study," J Am. Chem. Soc. 1990, 112, 4110-4120.
Yang, Wang-Jih., "Second Derivative and Fourier Self-Deconvolution approaches to Resolution Enhancement of Fourier Transform Infrared (FTIR) Spectra," 1981 International Conference on Fourier Transform Infrared Spectroscopy, 263-264, vol. 289, Bellingham, Wash.
Pistorius, Arthur, "Deconvolution as a Tool to Remove Fringes from an FT-IR Spectrum," Vibrational Spectroscopy 36, May 25, 2004, 89-95.
Saiani, A., "Self-Assembly and Gelation Properties of Alpha-Helix Versus Beta-Sheet Forming Peptides," Soft Matter—The Royal Society of Chemistry, 2009, 193-202, 5.
Caplan, Michael, "Self-Assembly of a Beta-Sheet Protein Governed by Relief of Electrostatic Repulsion Relative to van der Waals Attraction," Biomacromolecules, Jul. 19, 2000, 627-631, 1.
Aulisa, Ilorenzo, "Self-Assembly of Multidomain Peptides: Sequence Variation Allows Control over Cross-Linking and Viscoelasticity," Biomacromolecules, Jul. 23, 2009, 2694-2698, 10.
Kisiday, J., "self-Assembling Peptide Hydrogel Fosters Chondrocyte Extracellular Matrix Production and Cell Division: Implications for Cartilage Tissue Repair," Proceedings of the National Academy of Sciences of the USA, Jul. 23, 2002, 9996-100001, vol. 99.

(Continued)

*Primary Examiner* — Julie Ha
*Assistant Examiner* — Erinne Dabkowski
(74) *Attorney, Agent, or Firm* — Hovey Williams LLP

(57) ABSTRACT

The present invention broadly provides novel peptides that can be used to form hydrogels. The peptides are short (preferably 30 amino acid residues or less) and include hydrophilic and hydrophobic segments joined by a turning segment. The hydrogels are formed by altering the pH of a solution of these peptides to an acidic level, or by introducing a source of ions into a solution of these peptides. The resulting hydrogels are shear thinning gels that have high storage moduli and high rates of recovery after destruction. They find use in medical applications, including tissue engineering.

10 Claims, 22 Drawing Sheets

(56) References Cited

OTHER PUBLICATIONS

Pochan, Darrin, "Thermally Reversible Hydrogels via Intramolecular Folding and Consequent Self-Assembly of a de Novo Designated Peptide,"J. Am. Chem. Soc. Mar. 25, 2003, 11802-11803, 125.

Anderson, Daniel, "Smart Biomaterials," www.sciencemag.org, vol. 305, Sep. 24, 2004.

Skountzou, Ioanna, "Transcutaneous Immunization with Inactivated Influenza Virus Induces Protective Immune Responses," Vaccine 24, www.sciencedirect.com May 26, 2006, 6110-6119.

Shera, Jeanne, "Effects of Peptide Sequence on Surface Properties and Self-Assembly of an Amphiphilic pH-Responsive Peptide," Biomacromolecules, Jul. 30, 2009, 2446-2450, 10(9).

Scotter, Andrew, "Metal Ion-Dependent, Reversible, Protein Filament Formation by Designated Beta-Roll Polypeptides," BMC Structural Biology, www.biomedcentral.com, Oct. 1, 2007.

Hardy, John, "Polymeric Materials Based on Silk Proteins," www.elsevier.com/locate/polymer Aug. 9, 2008.

Banwell, Eleanor, "Rational Design and Application of Responsive Alpha-Helical Peptide Hydrogels," Nature Materials, Jun. 22, 2009, vol. 8.

Koutsonanos, Dimitrious, "Transdermal Influenza Immunization with Vaccine Coated Microneedle Arrays," PLOS One Journal, www.plosone.org, Mar. 2009, vol. 4, issue 3.

Lee, Kuen Young, "Hydrogels for Tissue Engineering," Chemical Reviews, American Chemical Society, Jul. 2001, vol. 101, No. 7.

Zhang, Shuguang, "Hydrogels wet or let die," Nature Materials, Jan. 2004, vol. 3.

Skountzou, Ioanna, "Incorporation of Glycosylphosphatidylinositol-Anchored Granulocyte-Macrophage Colony-Stimulating Factor or CD40 Ligand Enhances Immunogenicity of Chimeric Simian Immunodeficiency Virus-Like Particles," Journal of Virology, Feb. 2007, 1083-1094, vol. 81, No. 3.

Reed, Steven, "New Horizons in Adjuvants for Vaccine Development," Trends in Immunology, vol. 30, No. 1, Dec. 6, 2008.

Kazzaz, J., "Novel Anionic Microparticles Are a Potent Adjuvant for the Induction of Cytotoxic T Lymphocytes against recombinant p55 gag from HIV-1," Journal of Controlled Release 67, 2000, 347-356.

Nowak, Andrew, "Rapidly Recovering Hydrogel Scaffolds From Self-Assembling Diblock Copolypeptide Amphiphiles," Nature Journal, May 23, 2002, vol. 417.

Huang, Hongzhou, "Rational Design of Responsive Self-Assembling Peptides from Native Protein Sequences," Biomacromolecules, 3390-3394, vol. 11, Nov. 16, 2010.

Schneider, Joel, "Responsive Hydrogels from the Intramolecular Folding and Self-Assembly of a Designed Peptide," JACS Articles, Nov. 23, 2002.

Zawaneh, Peter, "Design of an Injectable Synthetic and Biodegradable Surgical Biomaterial," www.pnas.org, Apr. 6, 2010.

Salick, Daphne, "Design pf a Injectable β-Hairpin Peptide Hydrogel That Kills Methicillin-Resistant *Staphylococcus aureus*," Advance Materials, 2009, 4120-4123, vol. 21.

Langer, Robert, "Designing Materials for Biology and Medicine," Nature, Apr. 1, 2004, vol. 428.

Nemirovskiy, Olga, "Determination of Calcium Binding Sites in Gas-Phase Small Peptides bu Tandem Mass Spectrometry," J. Am. Soc. Mass Spectrom May 11, 1998, 1020-1028, vol. 9.

Zhang, Shuguang, "Fabrication of Novel Biomaterials Through Molecular Self-Assembly," Nature Biotechnology, Oct. 2003, vol. 21, No. 10.

Branco, Monica, "Fast Dynamics of Semiflexible Chain Networks of Self-Assembled Peptides," Biomolecules, 2009, 1374-1380, vol. 10.

Cushing, Melinda, "Hydrogel Cell Cultures," Science Magazine, May 25, 2007, vol. 316.

Zhang, Shuming, "A Self-Assembly Pathway to Aligned Monodomain Gels," Nature MaterialsJun. 13, 2010.

Cavalli, Silvia, "Amphiphilic Peptides and Their Cross-Disciplinary Role as Building Blocks for Nanoscience," Chemical Society Reviews, 2010, 214-263, vol. 39.

Jeong, Byeongmoon, "Biodegradable Block Copolymers as Injectable Drug-Delivery System," Nature, Aug. 28, 1997, vol. 388.

Koutsopoulos, Sotirios, "Controlled Release of Functional Proteins Through Designed self-Assembling Peptide Nanofiber Hydrogel Scaffold," www.pnas.org Mar. 24, 2009, 4623-4628, vol. 106, No. 12.

Mo, Xiaoqun, "Design of 11-Residue Peptides with Unusual Biophysical Properties: Induced Secondary Structure in the Absence of Water," Biophysical Journal, Mar. 1, 2008, 1807-1817, vol. 94, No. 5.

International Search Report and Written Opinion of the International Searching Authority dated Nov. 25, 2011 in corresponding PCT/US2011/027972 application.

* cited by examiner

SEQUENCE LISTING

<160> NUMBER OF SEQ ID NOS: 30

<210> SEQ ID NO 1
<211> LENGTH: 19
<212> TYPE: PRT
<213> ORGANISM: Artificial Sequence
<220> FEATURE:
<223> OTHER INFORMATION: Derivative of spider flagelliform silk protein
      and a trans-membrane segment of subunit IV in the dihydropyridine
      sensitive human muscle L-type calcium channel

<400> SEQUENCE: 1

Phe Leu Ile Val Ile Gly Ser Ile Ile Gly Pro Gly Gly Asp Gly Pro
1               5                   10                  15

Gly Gly Asp

<210> SEQ ID NO 2
<211> LENGTH: 10
<212> TYPE: PRT
<213> ORGANISM: Artificial Sequence
<220> FEATURE:
<223> OTHER INFORMATION: Derivative of spider flagelliform silk protein

<400> SEQUENCE: 2

Gly Pro Gly Gly Asp Gly Pro Gly Gly Asp
1               5                   10

<210> SEQ ID NO 3
<211> LENGTH: 4
<212> TYPE: PRT
<213> ORGANISM: Artificial Sequence
<220> FEATURE:
<223> OTHER INFORMATION: Peptide turning region derived from the third
      trans-membrane segment of subunit IV in the dihydropyridine
      sensitive human muscle L-type calcium channel
<220> FEATURE:
<221> NAME/KEY: MISC_FEATURE
<222> LOCATION: (1)..(1)
<223> OTHER INFORMATION: Xaa is G, I, or V
<220> FEATURE:
<221> NAME/KEY: MISC_FEATURE
<222> LOCATION: (3)..(4)
<223> OTHER INFORMATION: each Xaa is individually G, I, V, A, or L

<400> SEQUENCE: 3

Xaa Ser Xaa Xaa
1

<210> SEQ ID NO 4
<211> LENGTH: 5
<212> TYPE: PRT
<213> ORGANISM: Artificial Sequence
<220> FEATURE:
<223> OTHER INFORMATION: Hydrophobic region derived from the third
      trans-membrane segment of subunit IV in the dihydropyridine
      sensitive human muscle L-type calcium channel

<400> SEQUENCE: 4

Phe Leu Ile Val Ile
1               5

<210> SEQ ID NO 5
<211> LENGTH: 9
<212> TYPE: PRT
<213> ORGANISM: Artificial Sequence
<220> FEATURE:
<223> OTHER INFORMATION: Derivative of the third trans-membrane segment
      of subunit IV in the dihydropyridine sensitive human muscle L-type
      calcium channel.

<400> SEQUENCE: 5

Phe Leu Ile Val Ile Gly Ser Ile Ile
1               5

<210> SEQ ID NO 6
<211> LENGTH: 15
<212> TYPE: PRT
<213> ORGANISM: Artificial Sequence
<220> FEATURE:
<223> OTHER INFORMATION: Derivative of spider flagelliform silk protein
      and a trans-membrane segment of subunit IV in the dihydropyridine
      sensitive human muscle L-type calcium channel

<400> SEQUENCE: 6

Phe Leu Ile Val Ile Gly Pro Gly Gly Asp Gly Pro Gly Gly Asp
1               5                   10                  15

<210> SEQ ID NO 7
<211> LENGTH: 18
<212> TYPE: PRT
<213> ORGANISM: Artificial Sequence
<220> FEATURE:
<223> OTHER INFORMATION: Derivative of spider flagelliform silk protein
      and a trans-membrane segment of subunit IV in the dihydropyridine
      sensitive human muscle L-type calcium channel

<400> SEQUENCE: 7

Phe Leu Ile Val Ile Ser Ile Ile Gly Pro Gly Gly Asp Gly Pro Gly
1               5                   10                  15

Gly Asp

<210> SEQ ID NO 8
<211> LENGTH: 19
<212> TYPE: PRT
<213> ORGANISM: Artificial Sequence
<220> FEATURE:
<223> OTHER INFORMATION: Derivative of spider flagelliform silk protein
      and a trans-membrane segment of subunit IV in the dihydropyridine
      sensitive human muscle L-type calcium channel

<400> SEQUENCE: 8

Phe Leu Ile Val Ile Ile Ile Val Ile Gly Pro Gly Gly Asp Gly Pro
1               5                   10                  15

Gly Gly Asp

<210> SEQ ID NO 9
<211> LENGTH: 17
<212> TYPE: PRT
<213> ORGANISM: Artificial Sequence
<220> FEATURE:
<223> OTHER INFORMATION: Derivative of spider flagelliform silk protein
      and a trans-membrane segment of subunit IV in the dihydropyridine
      sensitive human muscle L-type calcium channel
<220> FEATURE:
<221> NAME/KEY: MISC_FEATURE
<222> LOCATION: (7)..(7)
<223> OTHER INFORMATION: Xaa is D-type Proline

<400> SEQUENCE: 9

Phe Leu Ile Val Ile Pro Xaa Gly Pro Gly Gly Asp Gly Pro Gly Gly
1               5                   10                  15

Asp

<210> SEQ ID NO 10
<211> LENGTH: 19

```
<212> TYPE: PRT
<213> ORGANISM: Artificial Sequence
<220> FEATURE:
<223> OTHER INFORMATION: Derivative of spider flagelliform silk protein
      and a trans-membrane segment of subunit IV in the dihydropyridine
      sensitive human muscle L-type calcium channel

<400> SEQUENCE: 10

Leu Leu Leu Leu Leu Gly Ser Ile Ile Gly Pro Gly Gly Asp Gly Pro
1               5                   10                  15

Gly Gly Asp

<210> SEQ ID NO 11
<211> LENGTH: 19
<212> TYPE: PRT
<213> ORGANISM: Artificial Sequence
<220> FEATURE:
<223> OTHER INFORMATION: Derivative of spider flagelliform silk protein
      and a trans-membrane segment of subunit IV in the dihydropyridine
      sensitive human muscle L-type calcium channel

<400> SEQUENCE: 11

Phe Leu Ile Val Ile Gly Ser Ile Ile Lys Lys Lys Lys Lys Lys
1               5                   10                  15

Lys Lys Lys

<210> SEQ ID NO 12
<211> LENGTH: 19
<212> TYPE: PRT
<213> ORGANISM: Artificial Sequence
<220> FEATURE:
<223> OTHER INFORMATION: Derivative of spider flagelliform silk protein
      and a trans-membrane segment of subunit IV in the dihydropyridine
      sensitive human muscle L-type calcium channel

<400> SEQUENCE: 12

Leu Leu Leu Leu Leu Gly Ser Ile Ile Lys Lys Lys Lys Lys Lys
1               5                   10                  15

Lys Lys Lys

<210> SEQ ID NO 13
<211> LENGTH: 10
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (4)..(4)
<223> OTHER INFORMATION: Xaa is G or A
<220> FEATURE:
<221> NAME/KEY: MISC_FEATURE
<222> LOCATION: (9)..(9)
<223> OTHER INFORMATION: Xaa is G or A

<400> SEQUENCE: 13

Gly Pro Gly Xaa Asp Gly Pro Gly Xaa Asp
1               5                   10

<210> SEQ ID NO 14
<211> LENGTH: 10
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (4)..(4)
```

```
<223> OTHER INFORMATION: Xaa is A, G, V, I, or L
<220> FEATURE:
<221> NAME/KEY: MISC_FEATURE
<222> LOCATION: (7)..(7)
<223> OTHER INFORMATION: Xaa is P, A, G, V, I, or L
<220> FEATURE:
<221> NAME/KEY: MISC_FEATURE
<222> LOCATION: (8)..(9)
<223> OTHER INFORMATION: each Xaa is individually A, G, V, I, or L

<400> SEQUENCE: 14

Gly Pro Gly Xaa Asp Gly Xaa Xaa Xaa Asp
1               5                   10

<210> SEQ ID NO 15
<211> LENGTH: 5
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: REPEAT
<222> LOCATION: (1)..(5)
<223> OTHER INFORMATION: 1 to 10 repeats
<220> FEATURE:
<221> NAME/KEY: MISC_FEATURE
<222> LOCATION: (4)..(4)
<223> OTHER INFORMATION: Xaa is G or A

<400> SEQUENCE: 15

Gly Pro Gly Xaa Asp
1               5

<210> SEQ ID NO 16
<211> LENGTH: 5
<212> TYPE: PRT
<213> ORGANISM: Artificial Sequence
<220> FEATURE:
<223> OTHER INFORMATION: Derivative of spider flagelliform silk protein
<220> FEATURE:
<221> NAME/KEY: MISC_FEATURE
<222> LOCATION: (4)..(4)
<223> OTHER INFORMATION: Xaa is A, G, V, I, or L

<400> SEQUENCE: 16

Gly Pro Gly Xaa Asp
1               5

<210> SEQ ID NO 17
<211> LENGTH: 4
<212> TYPE: PRT
<213> ORGANISM: Artificial Sequence
<220> FEATURE:
<223> OTHER INFORMATION: Synthesized peptide turning region

<400> SEQUENCE: 17

Gly Gly Gly Gly
1

<210> SEQ ID NO 18
<211> LENGTH: 4
<212> TYPE: PRT
<213> ORGANISM: Artificial Sequence
<220> FEATURE:
<223> OTHER INFORMATION: Synthesized peptide turning region
<220> FEATURE:
<221> NAME/KEY: MISC_FEATURE
<222> LOCATION: (2)..(2)
<223> OTHER INFORMATION: Ser can be substituted with T
<220> FEATURE:
<221> NAME/KEY: MISC_FEATURE
```

```
<222> LOCATION: (3)..(3)
<223> OTHER INFORMATION: Xaa is G, I, V, A, or L
<220> FEATURE:
<221> NAME/KEY: MISC_FEATURE
<222> LOCATION: (4)..(4)
<223> OTHER INFORMATION: Xaa is G, I, V, A, or L

<400> SEQUENCE: 18

Gly Ser Xaa Xaa
1

<210> SEQ ID NO 19
<211> LENGTH: 4
<212> TYPE: PRT
<213> ORGANISM: Artificial Sequence
<220> FEATURE:
<223> OTHER INFORMATION: Synthesized peptide turning region
<220> FEATURE:
<221> NAME/KEY: MISC_FEATURE
<222> LOCATION: (1)..(1)
<223> OTHER INFORMATION: Xaa is G, I, V, A, or L
<220> FEATURE:
<221> NAME/KEY: MISC_FEATURE
<222> LOCATION: (3)..(3)
<223> OTHER INFORMATION: Ser can be substituted with T
<220> FEATURE:
<221> NAME/KEY: MISC_FEATURE
<222> LOCATION: (4)..(4)
<223> OTHER INFORMATION: Xaa is G, I, V, A, or L

<400> SEQUENCE: 19

Xaa Gly Ser Xaa
1

<210> SEQ ID NO 20
<211> LENGTH: 4
<212> TYPE: PRT
<213> ORGANISM: Artificial Sequence
<220> FEATURE:
<223> OTHER INFORMATION: Synthesized peptide turning region
<220> FEATURE:
<221> NAME/KEY: MISC_FEATURE
<222> LOCATION: (1)..(1)
<223> OTHER INFORMATION: Xaa is G, I, V, A, or L
<220> FEATURE:
<221> NAME/KEY: MISC_FEATURE
<222> LOCATION: (2)..(2)
<223> OTHER INFORMATION: Xaa is G, I, V, A, or L
<220> FEATURE:
<221> NAME/KEY: MISC_FEATURE
<222> LOCATION: (4)..(4)
<223> OTHER INFORMATION: Ser can be substituted by T

<400> SEQUENCE: 20

Xaa Xaa Gly Ser
1

<210> SEQ ID NO 21
<211> LENGTH: 4
<212> TYPE: PRT
<213> ORGANISM: Artificial Sequence
<220> FEATURE:
<223> OTHER INFORMATION: Synthesized peptide turning region
<220> FEATURE:
<221> NAME/KEY: MISC_FEATURE
<222> LOCATION: (1)..(1)
<223> OTHER INFORMATION: Ser can be substituted by T
<220> FEATURE:
<221> NAME/KEY: MISC_FEATURE
<222> LOCATION: (3)..(3)
<223> OTHER INFORMATION: Xaa is G, I, V, A, or L
<220> FEATURE:
<221> NAME/KEY: MISC_FEATURE
```

```
<222> LOCATION: (4)..(4)
<223> OTHER INFORMATION: Xaa is G, I, V, A, or L

<400> SEQUENCE: 21

Ser Gly Xaa Xaa
1

<210> SEQ ID NO 22
<211> LENGTH: 4
<212> TYPE: PRT
<213> ORGANISM: Artificial Sequence
<220> FEATURE:
<223> OTHER INFORMATION: Synthesized peptide turning region
<220> FEATURE:
<221> NAME/KEY: MISC_FEATURE
<222> LOCATION: (1)..(1)
<223> OTHER INFORMATION: Xaa is G, I, V, A, or L
<220> FEATURE:
<221> NAME/KEY: MISC_FEATURE
<222> LOCATION: (2)..(2)
<223> OTHER INFORMATION: Ser can be substituted by T
<220> FEATURE:
<221> NAME/KEY: MISC_FEATURE
<222> LOCATION: (4)..(4)
<223> OTHER INFORMATION: Xaa is G, I, V, A, or L

<400> SEQUENCE: 22

Xaa Ser Gly Xaa
1

<210> SEQ ID NO 23
<211> LENGTH: 4
<212> TYPE: PRT
<213> ORGANISM: Artificial Sequence
<220> FEATURE:
<223> OTHER INFORMATION: Synthesized peptide turning region
<220> FEATURE:
<221> NAME/KEY: MISC_FEATURE
<222> LOCATION: (1)..(1)
<223> OTHER INFORMATION: Xaa is G, I, V, A, or L
<220> FEATURE:
<221> NAME/KEY: MISC_FEATURE
<222> LOCATION: (2)..(2)
<223> OTHER INFORMATION: Xaa is G, I, V, A, or L
<220> FEATURE:
<221> NAME/KEY: MISC_FEATURE
<222> LOCATION: (3)..(3)
<223> OTHER INFORMATION: Ser can be substituted by T

<400> SEQUENCE: 23

Xaa Xaa Ser Gly
1

<210> SEQ ID NO 24
<211> LENGTH: 4
<212> TYPE: PRT
<213> ORGANISM: Artificial Sequence
<220> FEATURE:
<223> OTHER INFORMATION: Synthesized peptide turning region
<220> FEATURE:
<221> NAME/KEY: MISC_FEATURE
<222> LOCATION: (2)..(2)
<223> OTHER INFORMATION: Xaa is G, I, V, A, or L
<220> FEATURE:
<221> NAME/KEY: MISC_FEATURE
<222> LOCATION: (3)..(3)
<223> OTHER INFORMATION: Ser can be substituted by T
<220> FEATURE:
<221> NAME/KEY: MISC_FEATURE
<222> LOCATION: (4)..(4)
<223> OTHER INFORMATION: Xaa is G, I, V, A, or L

<400> SEQUENCE: 24
```

```
Gly Xaa Ser Xaa
1

<210> SEQ ID NO 25
<211> LENGTH: 4
<212> TYPE: PRT
<213> ORGANISM: Artificial Sequence
<220> FEATURE:
<223> OTHER INFORMATION: Synthesized peptide turning region
<220> FEATURE:
<221> NAME/KEY: MISC_FEATURE
<222> LOCATION: (1)..(1)
<223> OTHER INFORMATION: Xaa is G, I, V, A, or L
<220> FEATURE:
<221> NAME/KEY: MISC_FEATURE
<222> LOCATION: (3)..(3)
<223> OTHER INFORMATION: Xaa is G, I, V, A, or L
<220> FEATURE:
<221> NAME/KEY: MISC_FEATURE
<222> LOCATION: (4)..(4)
<223> OTHER INFORMATION: Ser can be substituted by T

<400> SEQUENCE: 25

Xaa Gly Xaa Ser
1

<210> SEQ ID NO 26
<211> LENGTH: 4
<212> TYPE: PRT
<213> ORGANISM: Artificial Sequence
<220> FEATURE:
<223> OTHER INFORMATION: Synthesized peptide turning region
<220> FEATURE:
<221> NAME/KEY: MISC_FEATURE
<222> LOCATION: (1)..(1)
<223> OTHER INFORMATION: Ser can be substituted by T
<220> FEATURE:
<221> NAME/KEY: MISC_FEATURE
<222> LOCATION: (2)..(2)
<223> OTHER INFORMATION: Xaa is G, I, V, A, or L
<220> FEATURE:
<221> NAME/KEY: MISC_FEATURE
<222> LOCATION: (4)..(4)
<223> OTHER INFORMATION: Xaa is G, I, V, A, or L

<400> SEQUENCE: 26

Ser Xaa Gly Xaa
1

<210> SEQ ID NO 27
<211> LENGTH: 4
<212> TYPE: PRT
<213> ORGANISM: Artificial Sequence
<220> FEATURE:
<223> OTHER INFORMATION: Synthesized peptide turning region
<220> FEATURE:
<221> NAME/KEY: MISC_FEATURE
<222> LOCATION: (1)..(1)
<223> OTHER INFORMATION: Xaa is G, I, V, A, or L
<220> FEATURE:
<221> NAME/KEY: MISC_FEATURE
<222> LOCATION: (2)..(2)
<223> OTHER INFORMATION: Ser can be substituted by T
<220> FEATURE:
<221> NAME/KEY: MISC_FEATURE
<222> LOCATION: (3)..(3)
<223> OTHER INFORMATION: Xaa is G, I, V, A, or L

<400> SEQUENCE: 27

Xaa Ser Xaa Gly
1
```

```
<210> SEQ ID NO 28
<211> LENGTH: 4
<212> TYPE: PRT
<213> ORGANISM: Artificial Sequence
<220> FEATURE:
<223> OTHER INFORMATION: Synthesized peptide turning region
<220> FEATURE:
<221> NAME/KEY: MISC_FEATURE
<222> LOCATION: (2)..(2)
<223> OTHER INFORMATION: Xaa is G, I, V, A, or L
<220> FEATURE:
<221> NAME/KEY: MISC_FEATURE
<222> LOCATION: (3)..(3)
<223> OTHER INFORMATION: Xaa is G, I, V, A, or L
<220> FEATURE:
<221> NAME/KEY: MISC_FEATURE
<222> LOCATION: (4)..(4)
<223> OTHER INFORMATION: Ser can be substituted by T

<400> SEQUENCE: 28

Gly Xaa Xaa Ser
1

<210> SEQ ID NO 29
<211> LENGTH: 4
<212> TYPE: PRT
<213> ORGANISM: Artificial Sequence
<220> FEATURE:
<223> OTHER INFORMATION: Synthesized peptide turning region
<220> FEATURE:
<221> NAME/KEY: MISC_FEATURE
<222> LOCATION: (1)..(1)
<223> OTHER INFORMATION: Ser can be substituted by T
<220> FEATURE:
<221> NAME/KEY: MISC_FEATURE
<222> LOCATION: (2)..(2)
<223> OTHER INFORMATION: Xaa is G, I, V, A, or L
<220> FEATURE:
<221> NAME/KEY: MISC_FEATURE
<222> LOCATION: (3)..(3)
<223> OTHER INFORMATION: Xaa is G, I, V, A, or L

<400> SEQUENCE: 29

Ser Xaa Xaa Gly
1

<210> SEQ ID NO 30
<211> LENGTH: 4
<212> TYPE: PRT
<213> ORGANISM: Artificial Sequence
<220> FEATURE:
<223> OTHER INFORMATION: Peptide turning region derived from the third
      trans-membrane segment of subunit IV in the dihydropyridine
      sensitive human muscle L-type calcium channel

<400> SEQUENCE: 30

Gly Ser Ile Ile
1
```

PROTEIN PEPTIDE HYDROGELS

RELATED APPLICATIONS

The present application is the National Stage of International Application No. PCT/US2011/027972, filed Mar. 10, 2011, which claims the priority benefit of a provisional application entitled NOVEL PROTEIN PEPTIDE HYDROGELS, Ser. No. 61/312,323, filed Mar. 10, 2010, incorporated by reference herein.

SEQUENCE LISTING

The following application contains a sequence listing in computer readable format (CRF), submitted as a text file in ASCII format entitled "SequenceListing.txt," created on Mar. 10, 2011, as 6 KB. The contents of the CRF are hereby incorporated by reference.

BACKGROUND OF THE INVENTION

1. Field of the Invention

The present invention is concerned with novel peptides, hydrogels comprising those peptides, and methods of making such hydrogels.

2. Description of the Prior Art

Using peptide hydrogels as injectable materials for tissue engineering and other biotechnological applications has been an important discovery made over the past few decades. Because of its high water content and polymer network, peptide hydrogels are a promising material for storage and transfer of proteins without significant loss of their biological activity. A sol-gel transformation occurs when peptide molecules self-assemble into a well-defined nanofiber network that traps water molecules. Because this transformation occurs at specific temperatures and pHs, peptide hydrogel precursors may be injected into the body in the liquid phase and converted into hydrogels when physiological conditions (e.g., pH, temperature) change in vivo, which is important for injectable applications.

There is particularly a need for injectable hydrogels that are shear thinning and have rapid recovery characteristics. Such a hydrogel should have a storage modulus that decreases sharply under a shearing force, but that recover after the force is removed. The present invention meets this need.

SUMMARY OF THE INVENTION

The present invention is concerned with a peptide comprising the amino acid sequence FLIVIGSIIGPGGDGPGGD (SEQ ID NO:1), or a fragment or variant thereof having at least about 60% homology to this sequence.

In another embodiment, the peptide comprises the amino acid sequence GPGGDGPGGD (SEQ ID NO:2), or a fragment or variant thereof having at least about 60% homology to this sequence.

The invention further comprises a peptide comprising a hydrophobic region, a turning region, and a hydrophilic region, where the turning region is between the hydrophobic and hydrophilic regions, and the hydrophilic region is a peptide comprising the amino acid sequence GPGGDGPGGD (SEQ ID NO:2), or a fragment or variant thereof having at least about 60% homology to this sequence.

In a further embodiment, the invention includes a peptide comprising a turning region and at least one of a hydrophobic region or a hydrophilic region, where the turning region comprises amino acid residues $X^1SX^2X^2$ (SEQ ID NO:3), in any order, where: $X^1$ is selected from the group consisting of G, I, and V; each $X^2$ is individually selected from the group consisting of G, I, V, A, and L; and at least one of $X^1$ or $X^2$ is G.

The invention is also directed towards a gel comprising a peptide comprising a hydrophobic region, a turning region, and a hydrophilic region. The turning region is between the hydrophobic and hydrophilic regions.

Finally, the invention includes a method of forming a gel. The method comprises providing a peptide solution comprising at least about 0.1% by weight peptide, based upon the total weight of the solution taken as 100% by weight. The peptide comprises less than about 30 amino acid residues. At least one of the following is carried out:

(a) adjusting the pH of the solution to a level of from about 1 to about 6 so as to form the gel; or
(b) introducing a source of ions into the solution so as to form the gel, with the ions being selected from the group consisting of ions of Group I and Group II metals.

DETAILED DESCRIPTION OF THE PREFERRED EMBODIMENT

Inventive Peptides

Figure 1A:
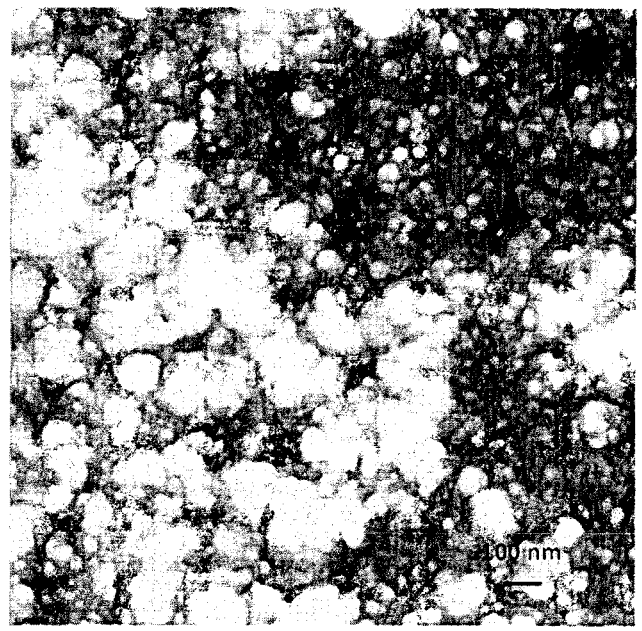
FIGS. 1a-1e shows transmission electron microscopy photographs (34,000×) of peptides in aqueous solutions.

The inventive peptides are amphiphilic and self-assembling, and preferably comprise three segments or regions: a hydrophobic region, a turning region, and a hydrophilic region. The turning region is positioned between, and preferably directed connected to, the hydrophobic and hydrophilic regions.

The hydrophobic region is preferably elastic and capable of binding the Group I and Group II metals (and particularly calcium). Preferred hydrophobic regions comprise from about 2 to about 15 amino acid residues, preferably from about 4 to about 9 amino acid residues, and more preferably about 5 amino acid residues. The amino acid residues are preferably selected from the group consisting of F, L, I, V, and A. (As used herein, it will be appreciated that when referring to amino acids that are present as part of a peptide, the amino acids are actually amino acid residues, regardless of whether "residues" is specifically stated.) In one embodiment, the hydrophobic region comprises, and preferably consists of, in any order, amino acid residues of FLIVI (SEQ ID NO:4). In another embodiment, the hydrophobic region comprises, and preferably consists of, in order, amino acid residues of FLIVI (SEQ ID NO:4).

Preferred hydrophilic regions comprise from about 5 to about 20 amino acid residues, preferably from about 5 to about 10 amino acid residues, and more preferably about 10 amino acid residues. More preferably, the hydrophilic regions comprise amino acid residues selected from the group consisting of G, P, D, V, I, L, and A. In one embodiment, the hydrophilic region comprises, and preferably consists of, in any order, amino acid residues of GPGXDGPGXD (SEQ ID NO:13), where X is selected from the group consisting of G and A. In another embodiment, the hydrophilic region comprises, and preferably consists of, in order, amino acid residues of GPGXDGPGXD (SEQ ID NO:13), where X is selected from the group consisting of G and A. In a further embodiment, the hydrophilic region comprises, and preferably consists of, in order or in any order, amino acid residues of $GPGX^1DGX^2X^1X^1D$ (SEQ ID NO:14), where each $X^1$ is individually selected from the group consisting of A, G, V, I, and L, and $X^2$ is selected from the group consisting of P, A, G, V, I, and L. In yet another embodiment, the hydrophilic region comprises amino acid residues of GPGXD (residues 1-5 of SEQ ID NO:14), where X is selected from the group consisting of A, G, V, I, and L. Furthermore, the hydrophilic region could be selected from the group consisting of amino acid residues of $[GPGX^1DGX^2X^1X^1D]_n$ (SEQ ID NO:14) and $[GPGXD]_n$ (residues 1-5 of SEQ ID NO:14), where n is from 1 to 10, and more preferably from 1 to 5.

The most preferred hydrophilic region comprises GPGGDGPGGD (SEQ ID NO:2) (in any order, but preferably in this order), or a fragment or variant having at least about 60% homology to this sequence. More preferably, the % homology to this sequence is at least about 80% and even more preferably at least about 90%.

Preferred turning regions comprise from about 4 to about 12 amino acid residues, preferably from about 4 to about 8 amino acid residues, and preferably 4 amino acid residues. The turning region of the inventive peptides preferably comprises amino acids residues selected from the group consisting of G, L, I, V, A, S, and T. One preferred turning region comprises, and preferably consists of, amino acid residues of $X^1SX^2X^2$ (SEQ ID NO:3), in any order (even more preferably in this order), where $X^1$ is selected from the group consisting of G, I, and V, with G being particularly preferred, and each $X^2$ is individually selected from the group consisting of G, I, V, A, and L, with I being particularly preferred. Preferably, at least one of $X^1$ or $X^2$ is G, with it being particularly preferred that at least $X^1$ is G. In one embodiment, S of $X^1SX^2X^2$ (SEQ ID NO:3) could be replaced with T.

The inventive peptides are preferably short peptides. That is, it is preferred that the inventive peptides have less than about 30 amino acid residues, more preferably less than about 20 amino acid residues, and even more preferably 19 amino acid residues. The most preferred peptide according to the invention comprises the amino acid sequence FLIVIGSIIGPGGDGPGGD (SEQ ID NO:1), or a fragment or variant thereof having at least about 60% homology to this sequence, more preferably at least about 80% homology to this sequence, and even more preferably at least about 90% homology to this sequence.

Finally, the inventive peptides will have a weight average molecular weight of from about 600 Da to about 4,500 Da, more preferably from about 1,000 Da to about 3,000 Da, and more preferably about 1,740 Da.

The inventive peptides can be prepared by microwave synthesizer, microbiosynthesis, fermentation, or genetic engineering technologies. A preferred method involves combining two native sequences from an elastic segment of spider silk and a trans-membrane segment of human muscle L-type calcium channel. More specifically, the most preferred hydrophilic region, GPGGDGPGGD (SEQ ID NO:2), is preferably designed from a n-spiral motif of spider flagelliform silk protein, while the most preferred hydrophobic and turning regions, FLIVIGSII (SEQ ID NO:5), are derived from the third trans-membrane segment of subunit IV in the dihydropyridine sensitive human muscle L-type calcium channel.

Methods of Forming Gels

The above peptides can be used to form gels, and particularly hydrogels. Advantageously, low levels of the peptides can be used to form these gels. The method involves forming or providing a solution of the peptide. The peptide is suspended, dispersed, or dissolved in a solvent (preferably water) at levels of at least about 0.1%, preferably from about 0.1% to about 5% by weight, more preferably from about 0.3% to about 3.5% by weight, and even more preferably from about 0.5% to about 2% by weight, based upon the total weight of the solution taken as 100% by weight. It is preferred that this peptide solution have a pH of from about 6 to about 12, and more preferably from about 8 to about 10.

There are two possible methods of forming the peptide solution into a gel. The first method comprises adjusting the pH of the solution to a level of from about 1 to about 6, preferably from about 2 to about 5, and more preferably from about 3 to about 4. This is referred to herein as the "pH adjustment method." This can be accomplished by known pH-adjusting methods, but the most preferred involves adding an acid selected from the group consisting of HCl, formic acid (HCOOH), acetic acid ($CH_3COOH$), HBr, and nitric acid ($HNO_3$) until such pH is achieved.

In the other method, a source of ions is introduced into the peptide solution, with preferred ions being selected from the group consisting of ions of Group I and Group II metals. This is referred to herein as the "ion trigger method." The most preferred Group I and Group II metal ions are selected from the group consisting of Ca, Na, Mg, K, and Zn ions. Exemplary sources of these ions include Group I and Group II metal chlorides, Group I and Group II metal bromides, Group I and Group II metal sulfides, Group I and Group II metal carbonates and bicarbonates.

The ion source should be introduced at levels so that the molar ratio of peptide to ion in the solution is from about 1:1 to about 1:100, preferably from about 1:5 to about 1:20, and more preferably about 1:10.

In either method, the gel is considered formed once G' (storage modulus) is greater than G" (storage loss).

Inventive Gels

The gels formed by the above methods have a uniform internetwork morphology with a porous structure and open cells. They typically comprise from about 0.1% to about 3% by weight of the peptide, preferably from about 0.25% to about 1.5% by weight of the peptide, and more preferably from about 0.5% to about 1% by weight of the peptide, based on the total weight of the gel taken as 100% by weight. The average cell size of the gel will be from about 10 μm to about 80 μm, preferably from about 20 μm to about 60 μm, and more preferably from about 30 μm to about 50 μm, as observed under a scanning electron microscope. Furthermore, the gel will comprise peptide nanofibers having an average diameter of from about 3 nm to about 30 nm, preferably from about 5 nm to about 20 nm, and more preferably from about 8 nm to about 15 nm, as measured under a transmission electron microscope. The gel will include peptide nanofibers having an average length of from about 0.3 μm to about 5 μm, preferably from about 0.8 μm to about 3 μm, and more preferably from about 1 μm to about 2 μm.

The inventive gels also possess a number of advantageous properties. The gels are shear thinning (i.e., the viscosity decreases with an increase in the rate of shear stress) when created by the ion trigger method. With either the ion trigger method or the pH adjustment method, the gels are very strong, having a storage modulus of at least about 500 Pa, preferably from about 800 Pa to about 3,000 Pa, and even more preferably from about 1,000 Pa to about 2,500 Pa at a peptide concentration of 0.85% and at room temperature (about 22° C.). The gels formed by the ion trigger method can achieve a storage modulus of at least about 800 Pa, preferably from about 900 Pa to about 1,500 Pa, and even more preferably from about 1,000 Pa to about 1,200 Pa at a peptide concentration of 0.85% and a temperature of 90° C. The gels formed by the pH adjustment method can achieve a storage modulus of at least about 800 Pa, preferably from about 900 Pa to about 1,500 Pa, and even more preferably from about 1,000 Pa to about 1,200 Pa at a peptide concentration of 0.85% and a temperature of 75° C.

After gel destruction, the gels have a % recovery of at least about 60%, preferably at least about 80%, more preferably at least about 90%, and even more preferably about 100% in less than about 10 minutes, preferably less than about 5 minutes, and more preferably less than about 2 minutes. A gel's % recovery is the % of the original (i.e., before gel destruction) storage modulus achieved by the gel after destruction.

The inventive gels are water soluble and temperature stable up to about 90° C. As used herein, "water soluble" means the gels can be diluted with water after formation, and "temperature stable" means that the hydrogel retains substantially all of its properties and is not denatured at temperatures ranging from about 1° C. to about 90° C.

The inventive gels can be used in biotechnology applications, including as scaffolds in tissue engineering.

EXAMPLES

The following examples set forth preferred methods in accordance with the invention. It is to be understood, however, that these examples are provided by way of illustration and nothing therein should be taken as a limitation upon the overall scope of the invention.

Materials and Methods

1. Peptide Synthesis

Peptides were synthesized on a CEM Liberty microwave peptide synthesizer (CEM Corporation, Matthews, N.C.) according to the automated base-labile 9-fluorenylmethoxycarbonyl (Fmoc) strategy with Fmoc-protected amino acids (EMD Biosciences, San Diego, Calif.). Peptides were cleaved using 95% trifluoroacetic acid (Sigma-Aldrich, Milwaukee, Wis.), 2.5% triisopropylsilane (Sigma), and 2.5% deionized water. After synthesis, peptides were washed three times with anhydrous ether (Fisher Biotech, Fair Lawn, N.J.), dissolved in acetonitrile and distilled (DI) water (50/50 v/v), and then freeze-dried. Molecular weight and purity of the synthesized peptides were confirmed by matrix-assisted laser desorption/ionization time-of-flight mass spectroscopy (Ultraflex II instrument, Bruker Daltronics, Billerica, Mass.) and high performance liquid chromatography (HPLC, Beckman Coulter, Inc., Fullerton, Calif.).

2. Hydrogel Preparation

The synthesized peptide was dissolved in dionized (DI) water to a concentration of 5 mM by adjusting the pH to 8.0-10.0 with 1 M NaOH (Sigma). The acidic h9e (see Table 3 below) hydrogel was prepared by adjusting the pH to 4.0 with 1 M HCl (Sigma). The h9e $Ca^{2+}$ hydrogel was prepared by adding $CaCl_2$ to the basic h9e peptide solution (molar ratio of peptide and $Ca^{2-}$ was 1:10, final pH was 7.0 to 9.0).

3. Transmission Electron Microscopy (TEM)

Peptide solutions were prepared on Formvar/carbon-coated 200-mesh copper grids (Electron Microscopy Sciences, Fort Washington, Pa.) and stained with 2% (w/v) uranyl acetate (Ladd Research Industries, Inc., Burlington, Vt.) for 60 seconds at ambient conditions before being imaged. The samples were imaged with a CM100 TEM (FEI Company, Hillsboro, Oreg.) at 100 kv.

4. Mass Spectrometry (MS)

MS experiments were performed using LTQ-Orbitrap (Thermo Electron Bremen, Germany) equipped with an electrospray ionization source. Samples were injected through a pulled fused silica capillary (50 μm ID) at a flow rate of 0.3 to 0.5 μL/min. using a spray voltage of 4 kV. The system was operated in the positive ion mode with a resolving power of 60,000 at m/z 400. MS/MS experiments were performed using a 2 to 3 amu isolation window. The collision energy was adjusted for each species to obtain about 70-90% fragmentation of the precursor ion. High-resolution mass analysis enabled unambiguous identification of the resulting fragments.

Stock solutions of peptides were prepared by dissolving 0.85 mg and 0.94 mg of h5e (MW 1370.6951) (see Table 3 below) and h9e (MW 1740.9167), respectively, in 500 μL HPLC grade water and adding 60 to 80 μL of 0.25 M NaOH to obtain solutions with a pH of 8. Solutions for MS experiments were prepared by mixing 10 μL of the stock solution with 10 μl of 0.1 M $CaCl_2$ and adding 200 μl of 50:50 (v:v) H2O/acetonitrile.

5. Circular Dichroism (CD) Experiments

The CD spectra of h9e acidic hydrogel, and $Ca^{2+}$ hydrogel were recorded at ambient conditions using a Jasco J-815 Spectrometer (Jasco Corporation, Tokyo, Japan). The concentrations of the samples were 1 mM (0.17 wt %). CD spectra were recorded from 190 to 260 nm with 1 nm bandwidth and 20 nm min⁻ scanning speed, then averaged over two accumulations. Baselines were recorded using basic, acidic, and $Ca^{2+}$ solutions without peptide.

6. Fourier Transform Infrared Spectroscopy (FTIR)

The $Ca^{2+}$ and acidic hydrogels of h9e were prepared and freeze-dried. The FTIR spectra were recorded on a PerkinElmer spectrum 400 FT-IR/FT-NIR spectrometer (PerkinElmer Inc., Waltham, Mass.) in the range of wavenumbers from 400-4000 $cm^{-1}$. The accumulation was 16 sans, and the peaks were identified by deconvolution.

7. Rheology

The storage, G', and loss, G", moduli of h9e acidic and $Ca^{2+}$ hydrogels were determined on a rheometer system C-VOR 150 (Malvern instruments, Malvern, Worcestershire WR141XZ, United Kingdom) with a 20-mm diameter parallel plate geometry through frequency sweep (strain 1%, frequency 0.01 to 10 Hz, temperature 25° C.), amplitude sweep (strain 1 to 500%, frequency 1 Hz, temperature 25° C.), and temperature profile (strain 1%, frequency 1 Hz, Temperature 5° C., 20° C., 37° C., 50° C., 75° C., and 90° C.) measurements. The multiple amplitude sweep experiments were conducted to test the moduli recovery of peptide hydrogels. The time gap between every two tests was 10, 30, and 60 seconds for h9e $Ca^{2+}$ hydrogel.

Results and Discussion

The h5e and h9e peptides were each dissolved in separate 100 mM NaOH solutions and examined with TEM. Short fiber integrations were observed in the h5e solution (see FIG. 1a), while the h9e solution contained predominantly dimers of needle-shape nanofibers of about 10 nm width (see FIG. 1e). Changing the pH value to acidic or adding $Ca^{2+}$ solution made the h5le solution become cloudy with sedimentation. The h5e molecules aggregated into large insoluble particles that could be observed with the naked eye.

Changing the pH value to acidic or adding $Ca^{2+}$ solution to the h9e solution produced two different kinds of hydrogel. These significantly different behaviors between these two peptides were unexpected. In comparing their primary structures, beside the hydrophobic core h5 and the fiber structure induced region $eD_2$ (GPGGDGPGGD (SEQ ID NO:2)), the turning segment GSII (residues 6-9 of SEQ ID NO:5) was the only difference in the sequence of h5e and h9e, indicating it plays a key role in hydrogel formation.

Figure 2:
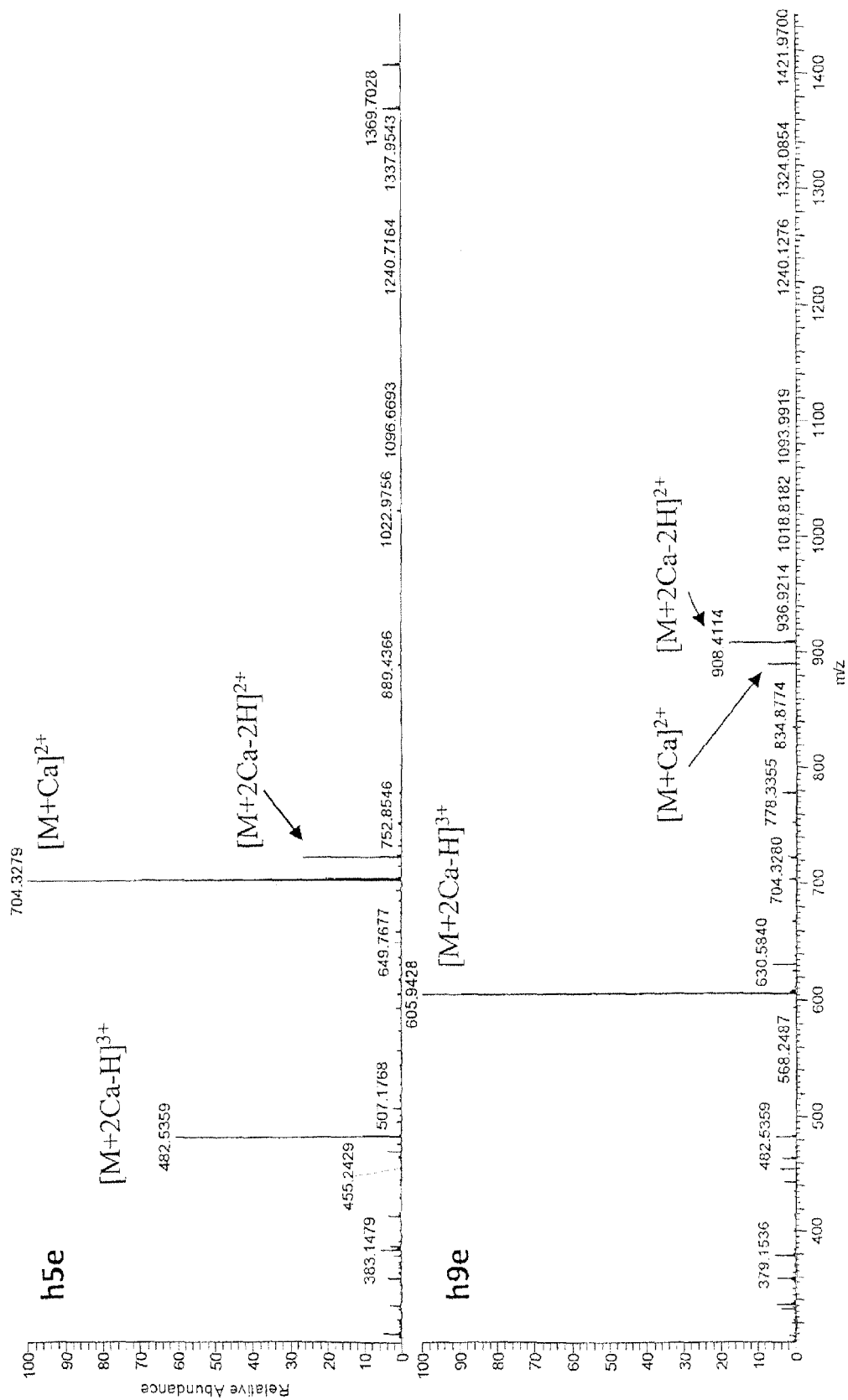
FIG. 2 depicts graphs of the MS fragments of h5e and h9e peptides.

MS experiments were conducted to identify possible precursors of the peptide assembly and nanofiber crossing in a $Ca^{2+}$ solution of h5e and h9e peptides (see FIG. 2). Mass spectra obtained for both peptides were dominated by $Ca^{2+}$ adducts, indicating a high affinity of h5e and h9e to calcium.

Figure 3A:
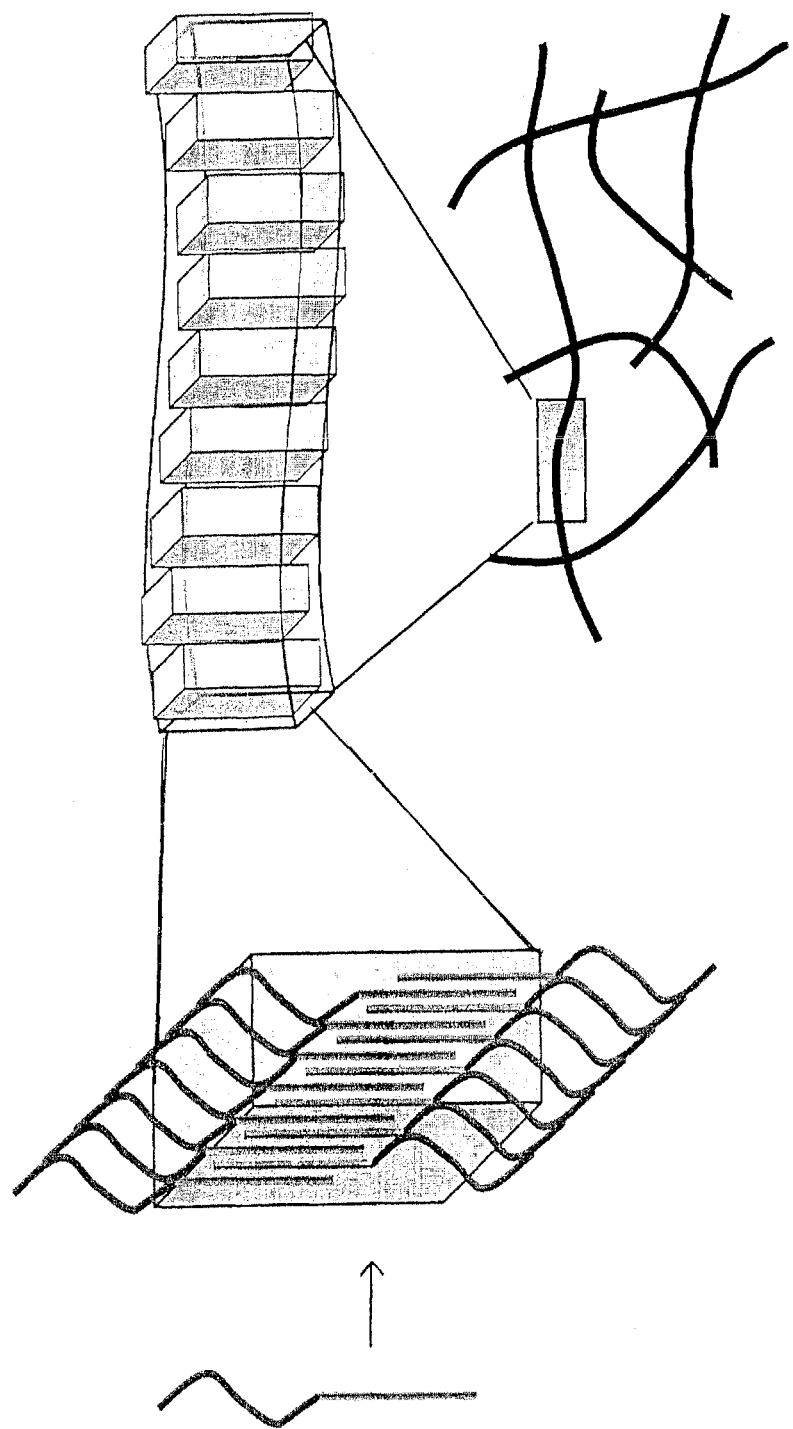
FIG. 3a-3c schematically depicts the assembly of a linear peptide, a peptide with a flexible turning segment, and a sharp turning peptide.
Figure 3B:
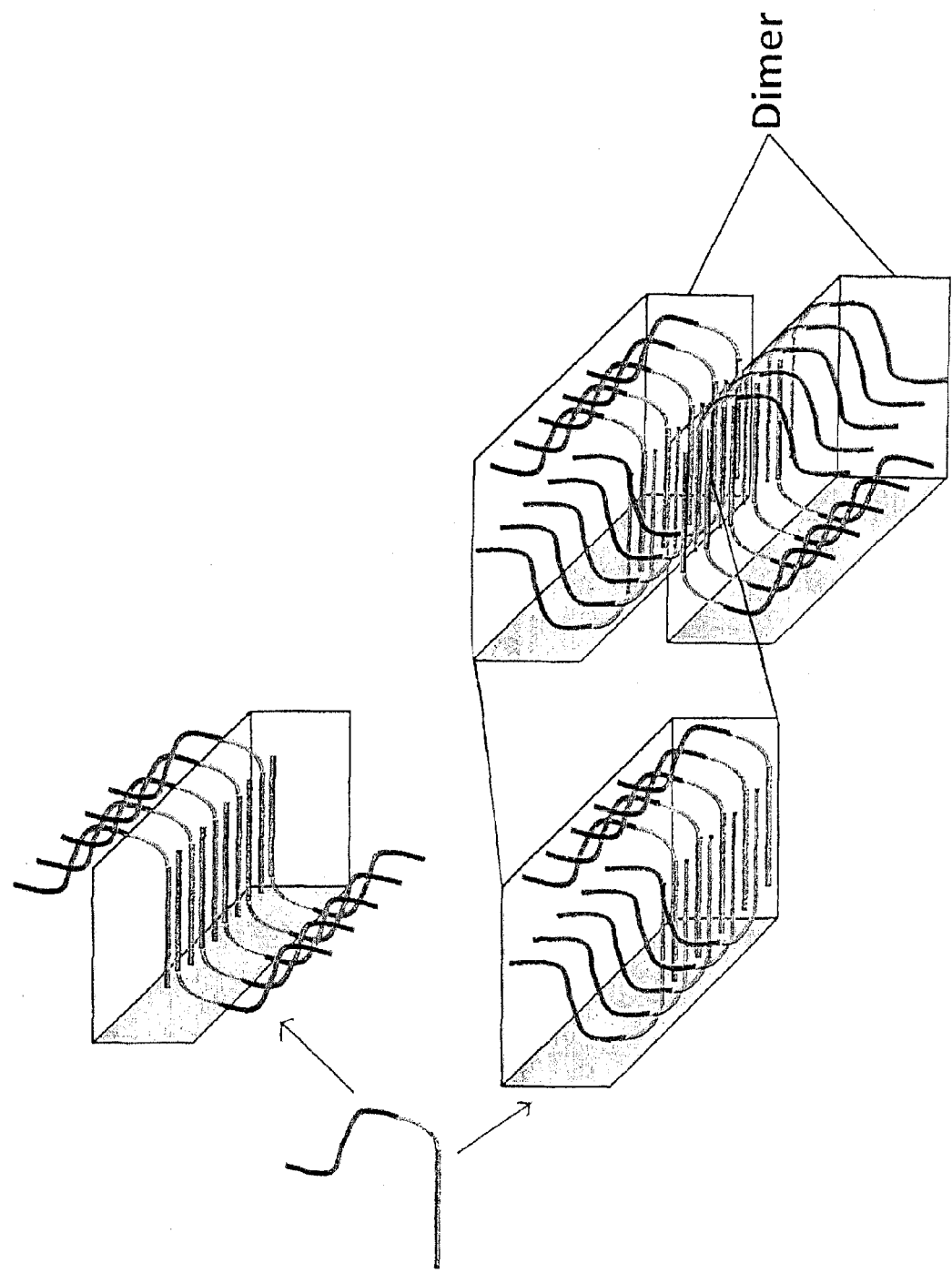

MS/MS experiments were conducted to gain insight on the mode of binding of calcium to h5e and h9e peptides. Fragmentation of peptide molecules cationized on calcium produced a number of backbone fragments including y-, b-, a-, z- and c-ions. (As will be understood by one of ordinary skill in the art, the N-terminal sequence ions contain the amino terminus and are labeled "a" to "c," while the C-terminal sequence ions contain the carboxylate terminus and are labeled from x to z.) The a-ion formation is promoted by calcium binding and occurs C-terminal to the $Ca^{2+}$ binding site. Examination of the MS/MS spectra obtained for different calcium adducts of the h5e and h9e peptides (Tables 1, 2) shows that in $[M+Ca]^{2+}$ ion, calcium is most likely coordinated by the carboxyl group of the internal D residue and is solvated by the C-terminal D. Fragmentation behavior changed in an interesting way for $[h9e+2Ca]^{4+}$ (Table 1). Cleavages indicative of $Ca^{2+}$ binding were observed in the SII and GDGPG (residues 4-8 of SEQ ID NO:2) regions, suggesting that although the first $Ca^{2+}$ is bound to the internal D residue, the second one is coordinated by serine. Differences in $Ca^{2+}$ binding capacity of the two peptides indicated the different assembly pathways. The tight, $Ca^{2+}$-binding h9e has a more compact structure and less hydrophobic area exposure than h5e (FIGS. 3a and 3b), which may explain the morphological difference of their supramolecular aggregation and why a hydrogel formed in h9e but not h5e.

TABLE 1

Fragmentation behavior of several precursor ions observed in the ESI spectra of the h5e peptide (M)

| Precursor | | $[M + H + Ca]^{3+}$ (m/z 469.891) | | $[M + 2Ca - H]^{3+}$ (m/z 482.54) | | $[M + Ca]^{2+}$ (m/z 704.33) | |
|---|---|---|---|---|---|---|---|
| Fragments | | N-terminal | C-terminal | N-terminal | C-terminal | N-terminal | C-terminal |
| 1 | F | | | | | | |
| 2 | L | $a_2; b_2{}^{a)}$ | $[y_{14} - H + Ca]^{2+}$ | $a_2; b_2$ | $[y_{14} - 3H + 2Ca]^{2+}$ | $a_2$ | |
| 3 | I | $b_3$ | $[y_{13} - H + Ca]^{2+}$ | | $[y_{13} - 3H + 2Ca]^{2+}$ $[y_{13} - 3H + 2Ca - H_2O]^{2+}$ | $b_3$ | |
| 4 | V | | $[y_{12} - H + Ca]^{2+}$ | | $[y_{12} - 3H + 2Ca]^{2+}$ | $a_4; b_4$ | $[y_{12} - H_2O - 2H + Ca]^+$ |
| 5 | I | | | | | | $[y_{11} - H_2O - 2H + Ca]^+$ |
| 6 | G | | $[y_{10} - H + Ca]^{2+}$ | | | | $[y_{10} - 2H + Ca]^+$ $[y_{10} - H_2O - 2H + Ca]^+$ |
| 7 | P | | | | | | $[y_9 - H_2O - 2H + Ca]^+$ |
| 8 | G | | | | | $[b_8 - 2H + Ca]^+$ | |
| 9 | G | | | | $[c_9 - H + Ca]^{2+}$ | $[c_9 - H + Ca]^{2+}$ $[c_9 - 2H + Ca]^+$ | |
| 10 | D | | | | | $[b_{10} - H + Ca]^{2+}$ $[a_{10} - H + Ca]^{2+}$ $[b_{10} - 2H + Ca]^+$ $[c_{10} - 2H + Ca]^+$ | |
| 11 | G | | | | | $[b_{11} - 2H + Ca]^+$ | $y_5$ $[y_5 - H + Ca]^+$ |

TABLE 1-continued

Fragmentation behavior of several precursor ions observed in the ESI spectra of the h5e peptide (M)

| Precursor | [M + H + Ca]$^{3+}$ (m/z 469.891) | | [M + 2Ca - H]$^{3+}$ (m/z 482.54) | | [M + Ca]$^{2+}$ (m/z 704.33) | |
|---|---|---|---|---|---|---|
| Fragments | N-terminal | C-terminal | N-terminal | C-terminal | N-terminal | C-terminal |
| 12  P | | | | | [b$_{12}$ – H + Ca]$^+$ | y$_4$ |
| 13  G | [b$_{13}$ – H + Ca]$^{2+}$ | | | | [b$_{13}$ – H + Ca]$^{2+}$ | |
| 14  G | [b$_{14}$ – H + Ca]$^{2+}$ | | | | [b$_{14}$ - H + Ca]$^{2+}$ | |
| | | | | | [a$_{14}$ – H + Ca]$^{2+}$ | |
| 15  D | | | | | | |

$^{a)}$Abundant fragments are shown in bold

TABLE 2

Fragmentation behavior of several precursor ions observed in the ESI spectra of the h9e peptide (M)

| Precursor | [M + 2Ca - H]$^{3+}$ (m/z 605.948) | | [M + H + Ca]$^{3+}$ (m/z 593.299) | | [M + Ca]$^{2+}$ (m/z 889.444) | | [M + Ca]$^{4+}$ (m/z 454.713) | |
|---|---|---|---|---|---|---|---|---|
| Fragments | N-terminal | C-terminal | N-terminal | C-terminal | N-terminal | C-terminal | N-terminal | C-terminal |
| 1  F | | | | | | | | |
| 2  L | a$_2$; b$_2$ | [y$_{18}$ + 2Ca – 3H]$^{2+}$ | a$_2$; b$_2$ | [y$_{18}$ + Ca – H]$^{2+}$ | | | a$_2$ | |
| 3  I | b$_3$ | [y$_{17}$ + 2Ca - 3H]$^{2+}$ | b$_3$ | [y$_{17}$ + Ca - H]$^{2+}$ | b$_3$ | | b$_3$ | |
| | | | | [z$_{17}$ + 2Ca – 2H]$^{2+}$ | | | | |
| 4  V | b$_4$ | [y$_{16}$ + 2Ca - 3H]$^{2+}$ | b$_4$ | [y$_{16}$ + Ca - H]$^{2+}$ | b$_4$ | | a$_4$; b$_4$ | [y$_{16}$ + 2Ca – 3H]$^{2+}$ |
| 5  I | | [y$_{15}$ + 2Ca - 3H]$^{2+}$ | | [y$_{15}$ + Ca – H]$^{2+}$ | | | | [y$_{15}$ + 2Ca – 3H]$^{2+}$ |
| 6  G | | [y$_{14}$ + 2Ca – 3H]$^{2+}$ | | | | | | [y$_{14}$ + 2Ca – 2H]$^{2+}$ |
| | | | | | | | | [y$_{14}$ + 2Ca – 3H – H$_2$O]$^{2+}$ |
| | | | | | | | | [y$_{14}$ + 2Ca - 3H]$^{2+}$ |
| 7  S | | | | | | [a$_7$ + Ca – 3H]$^{2+}$ | | [y$_{13}$ + 2Ca – 3H]$^{2+}$ |
| | | | | | | [a$_7$ + Ca - H]$^{2+}$ | | |
| | | | | | | [b$_7$ + Ca - H]$^{2+}$ | | |
| 8  I | | | | | | | | [y$_{12}$ + Ca – H]$^{2+}$ |
| | | | | | | | | [y$_{12}$ + 2Ca – 3H]$^{2+}$ |
| 9  I | | | | | | | | |
| 10  G | | | | | | [b$_{10}$ - H + Ca]$^{2+}$ | | |
| 11  P | | | | | | | | |
| 12  G | | | | | | | | |
| 13  G | | | | [a$_{13}$ + Ca – H]$^{2+}$ | | | | |
| | | | | [b$_{13}$ + Ca – H]$^{2+}$ | | | | |
| | | | | [c$_{13}$ + Ca – H]$^{2+}$ | | | | |
| 14  D | | | | | | [b$_{14}$ + Ca - H]$^{2+}$ | | [b$_{14}$ – H + Ca]$^{2+}$ |
| | | | | | | [b$_{14}$ + Ca – H – H$_2$O]$^{2+}$ | | |
| 15  G | | | | [b$_{15}$ + Ca – H]$^{2+}$ | | | | [y$_5$ + Ca - H]$^{2+}$ |
| 16  P | | | | | | | | |
| 17  G | | | | | | | | |
| 18  G | | | | [b$_{18}$ + Ca – H]$^{2+}$ | | | | |
| 19  D | | | | | | | | |

To further understand the contribution of each sequence region for hydrogel formation, the h9e sequence was divided into three regions: the relatively hydrophobic part FLIVI (SEQ ID NO:4); the relatively hydrophilic part GPGGDG-PGD (SEQ ID NO:2); and the critical GSII segment (residues 6-9 of SEQ ID NO:5). A series of peptides was also designed by modifying each region (Table 3).

TABLE 3

| PEPTIDE | SEQUENCE | IN CA$^{2+}$ SOLUTION OR ACIDIC SOLUTION |
|---|---|---|
| h5e | FLIVI-GPGGDGPGGD (SEQ ID NO: 6) | insoluble particles |
| h9e | FLIVI-GSII-GPGGDGPGGD (SEQ ID NO: 1) | strong hydrogel |
| h5SIIe | FLIVI-SII-GPGGDGPGGD (SEQ ID NO: 7) | gel-like particles |
| h5IIVIe | FLIVI-IIVI-GPGGDGPGGD (SEQ ID NO: 8) | insoluble particles |
| h5PP$^D$e | FLIVI-PP$^D$-GPGGDGPGGD (SEQ ID NO: 9) | liquid |

TABLE 3-continued

| PEPTIDE | SEQUENCE | IN $Ca^{2+}$ SOLUTION OR ACIDIC SOLUTION |
|---|---|---|
| L5GSIIe | LLLLL-GSII-GPGGDGPGGD (SEQ ID NO: 10) | weak hydrogel |
| h5GSIIK | FLIVI-GSII-KKKKKKKKKK (SEQ ID NO: 11) | weak hydrogel |
| L5GSIIK10 | LLLLL-GSII-KKKKKKKKKK (SEQ ID NO: 12) | no hydrogel |

Figure 1B:
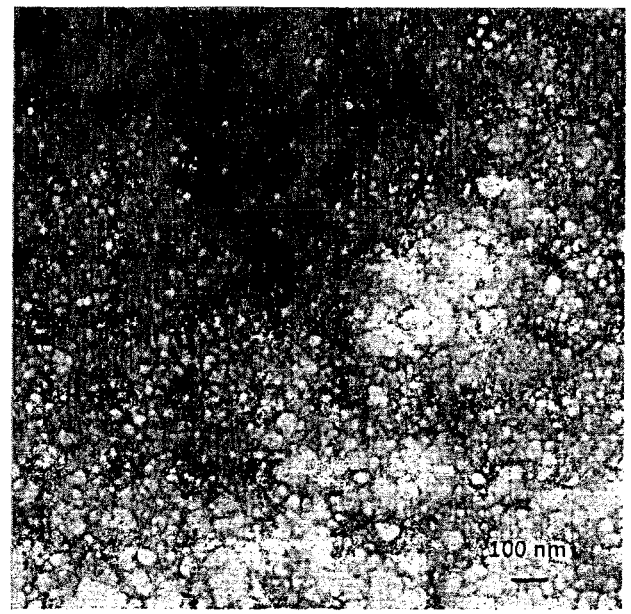

The peptide h5SIIe, designed by removing the glycine residue from the GSII segment, exhibited short fiber integrations in aqueous solution (see FIG. 1b). Unlike the hydrogel of h9e or insoluble particles of h5e, h5SIIe aggregated into gel-like particles in the presence of $Ca^{2+}$ or in an acidic solution. This phenomenon suggested that the conformation freedom provided by the glycine residue should be another critical factor for peptide correct assembly.

Figure 1C:
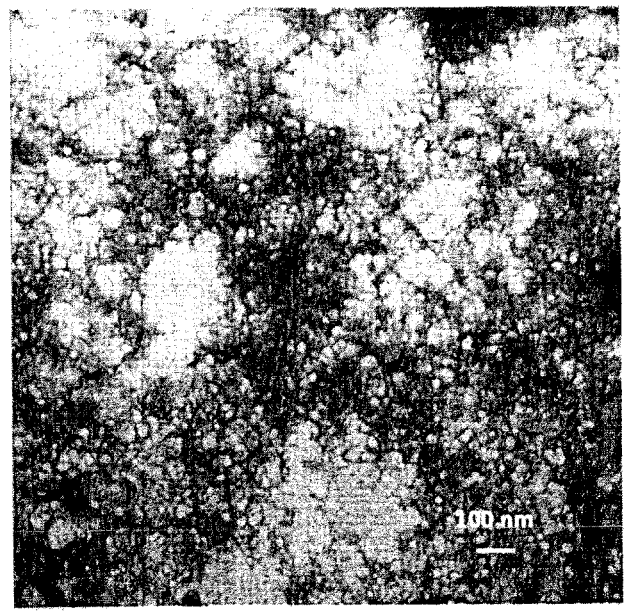
Figure 1D:
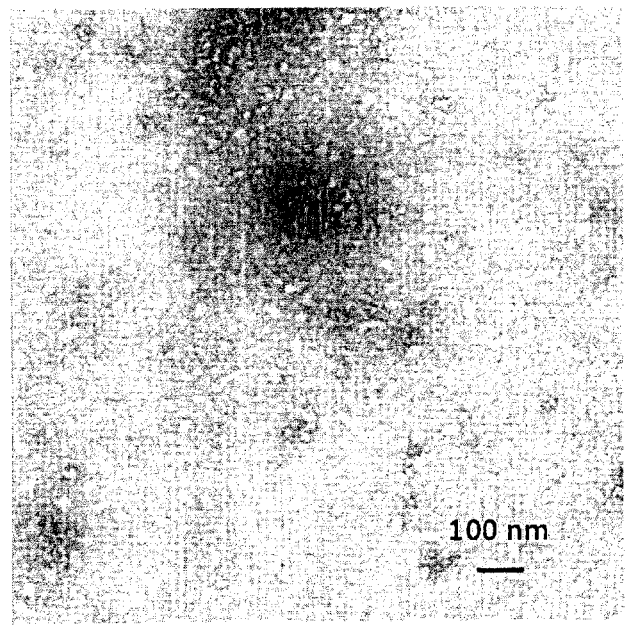
Figure 1E:
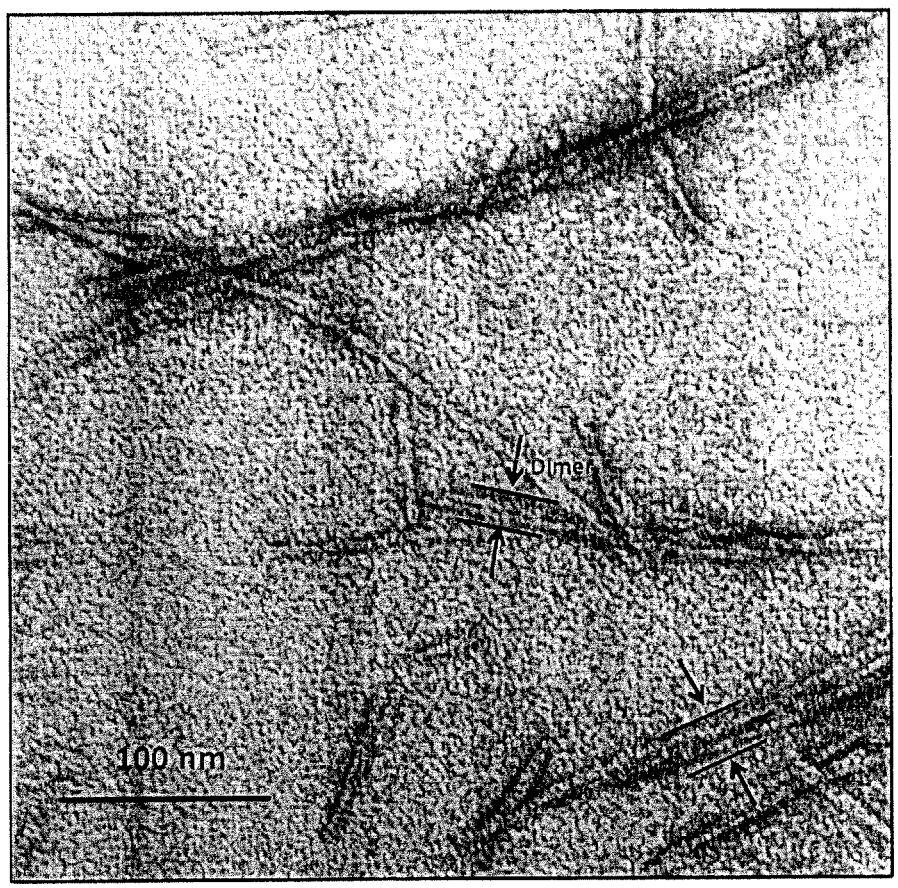
Figure 3C:
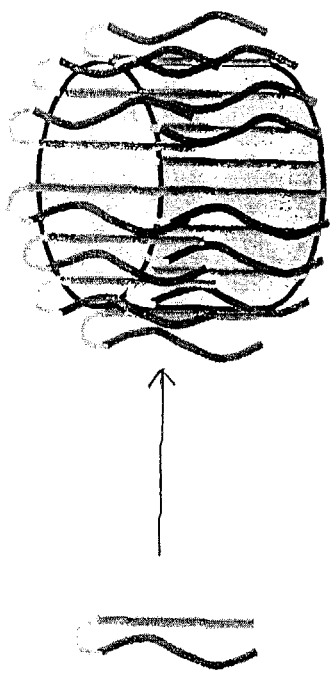

Next, two relatively inflexible segments, IIVI (residues 6-9 of SEQ ID NO:8) and $PP^D$, were selected to replace the GSII (residues 6-9 of SEQ ID NO:1) segment for peptides h5IIVIe and h5PP$^D$e. IIVI (residues 6-9 of SEQ ID NO:8) is a hydrophobic and linear structure, but $PP^D$ is a sharp-turning motif. The peptide h5IIVIe has a similar morphology as h5e (see FIG. 1c), and becomes insoluble particles in the presence of $Ca^{2+}$ or in an acidic solution. Surprisingly, the peptide h5PP$^D$e was soluble in neutral water without any pH adjustment. The small amorphous morphology and spherical aggregation presented in TEM images of h5PP$^D$e (see FIG. 1d) indicate the spherical assembly of peptide molecules when the sharp turning h5PP$^D$e fold the hydrophobic region and the hydrophilic region as a hairpin structure (FIG. 3c). Except for h9e, none of these peptides formed a hydrogel. Both the correct packing of the peptide monomers with metal ions and the conformation freedom between the hydrophobic and hydrophilic segments of peptides played important roles for hydrogel forming capability.

Figure 4:
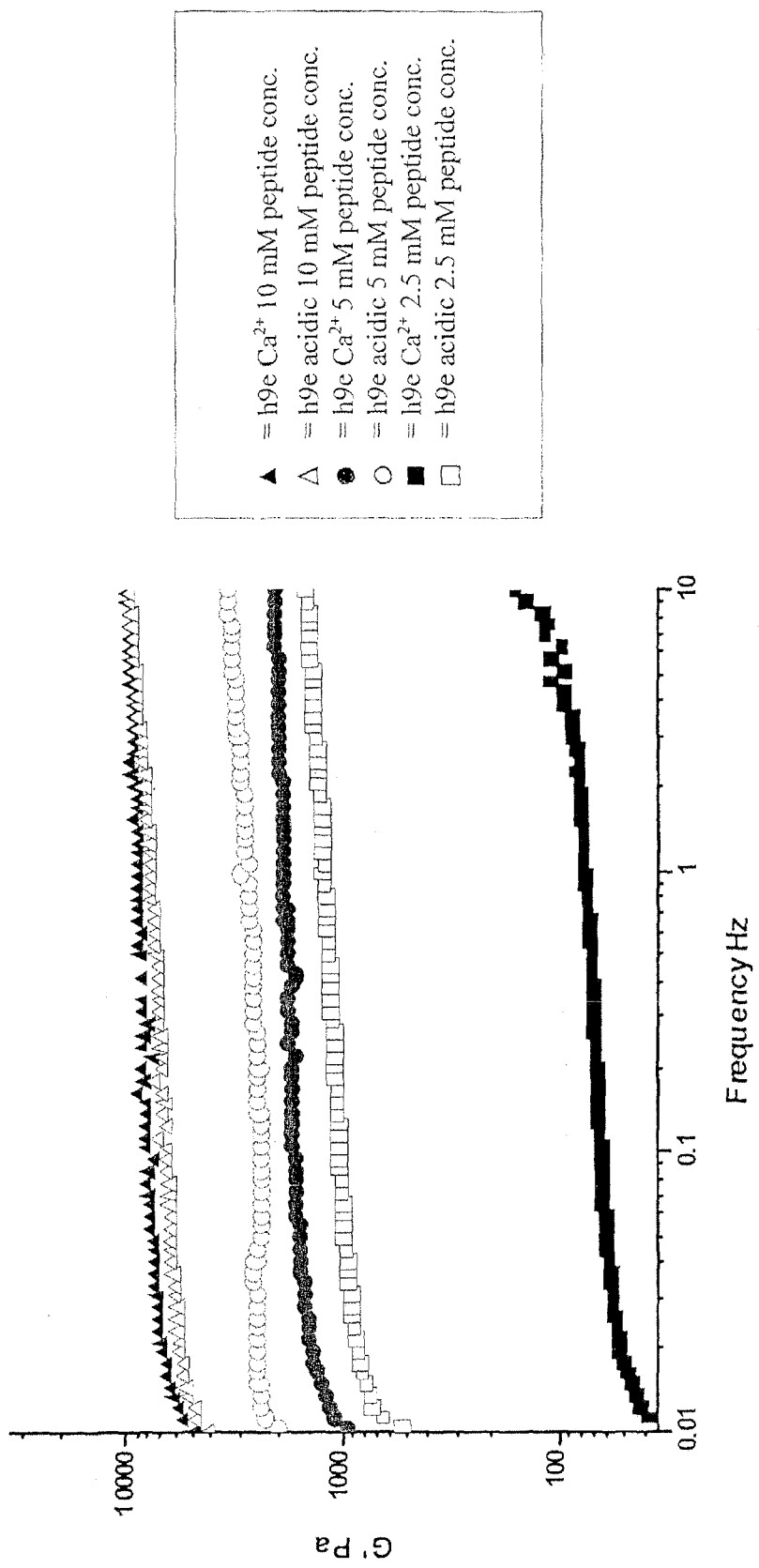
FIG. 4 is a graph showing G' of the h9eCa$^{2+}$ (solid) and h9e (open) acidic hydrogels.

In addition, two other peptides, L5GSIIe and h5GSIIK10, were designed by retaining the GSII (residues 6-9 of SEQ ID NO:1) motif and substituting the h5 segment of h9e with LLLLL (residues 1-5 of SEQ ID NO:10), or replacing the eD$_2$ segment of h9e with KKKKKKKKKK (residues 1-10 of SEQ ID NO:11), respectively. These two sequences formed weak hydrogels. The storage modulus of 5 mM of L5GSIIe was 21.6±0.3 Pa in $Ca^{2+}$ solution and that of 5 mM h5GSIIK10 was 55.0±0.9 Pa in basic pH, both of which were much smaller than the storage modulus of the h9e hydrogel, 1560.0±13.0 Pa (h9e $Ca^{2+}$ hydrogel) and 2863.7±27.8 Pa (h9e acidic hydrogel), formed at the same concentration (FIG. 4). When both the h5 and eD$_2$ segments of h9e were replaced, the peptide L5GSIIK10 did not form a hydrogel in aqueous solution. These findings suggest that h9e, designed from rational combination of two native segments, is a unique hydrogel-forming sequence.

Figure 5A:
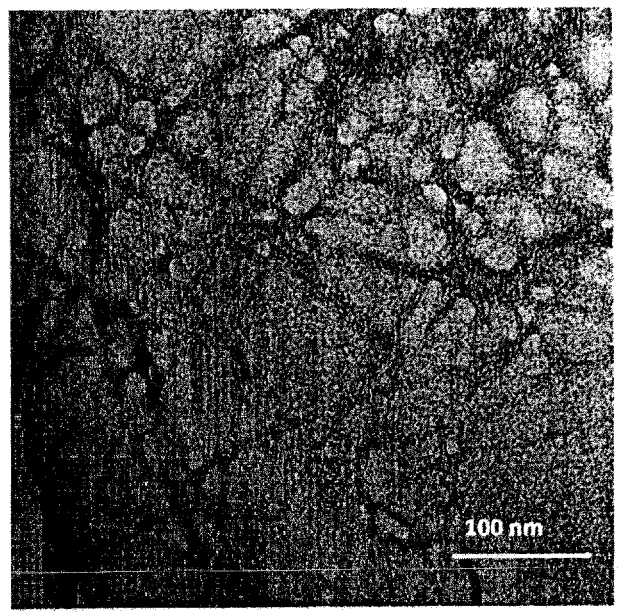
FIG. 5a-f are transmission electron microscopy photographs (130,000×) showing the morphological and structural properties of h9eCa$^+$ and acidic hydrogels.
Figure 5B:
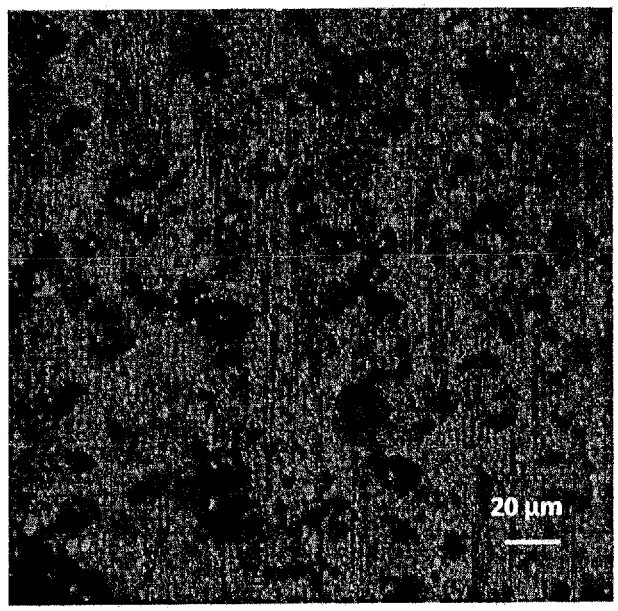
Figure 5C:
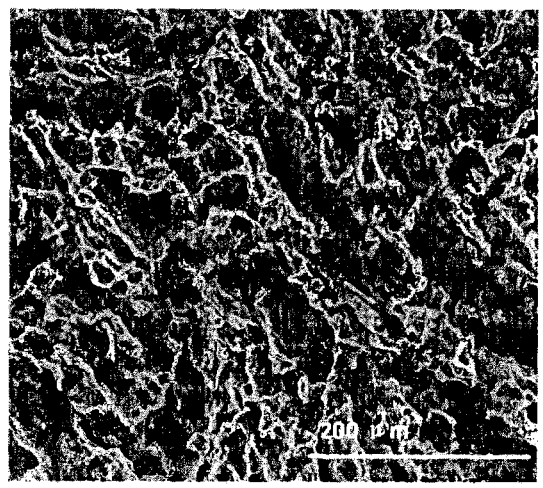
Figure 5D:
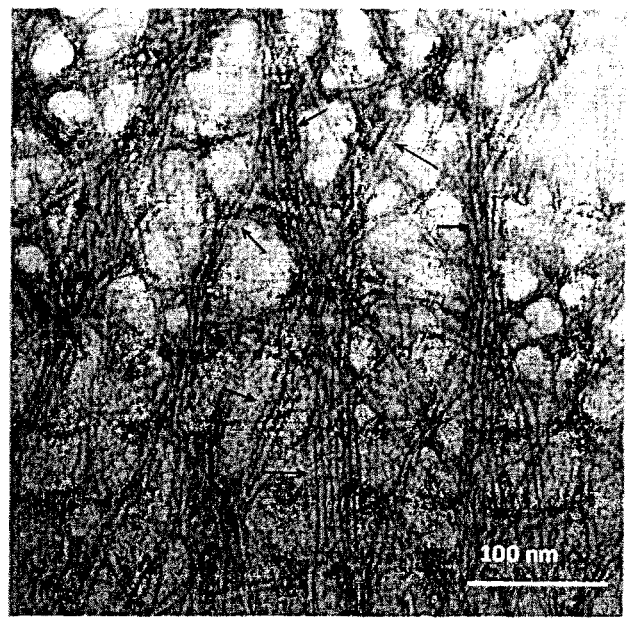
Figure 5E:
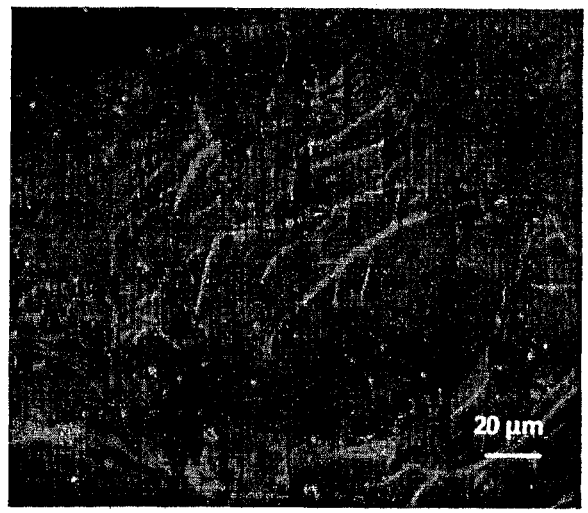
Figure 5F:
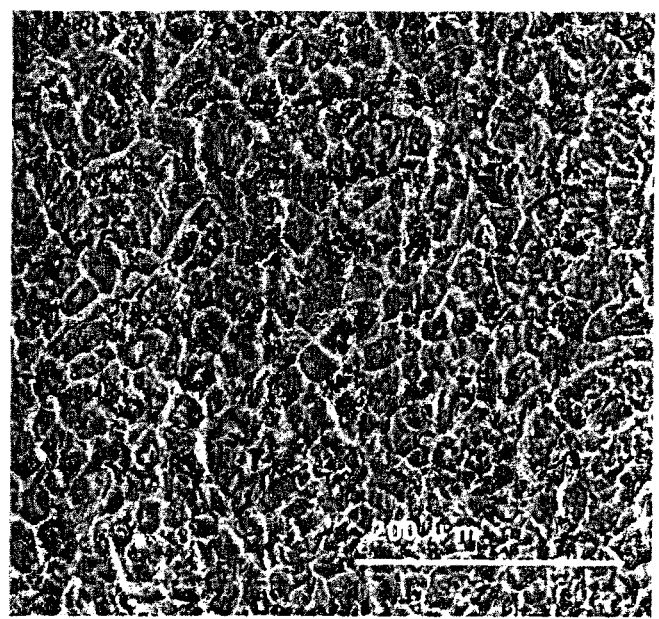
Figure 6:
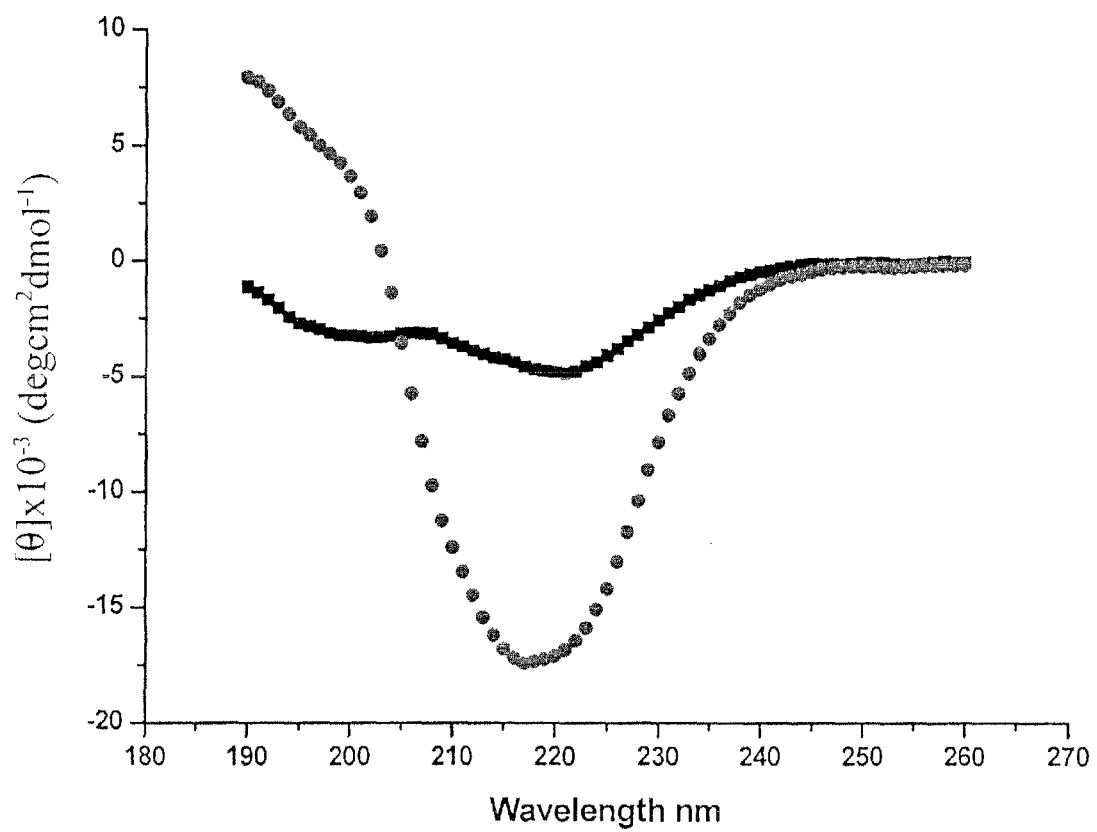
FIG. 6 is a graph showing the CD spectra of h9eCa$^{2+}$ (gray) and h9e acidic (black) hydrogels.

The h9e formed hydrogels in $Ca^{2+}$ solution as well as at an acidic pH. The needle-shaped nanofibers (about 10 nm width) were extended and crossed as fiber-networks in a $Ca^{2+}$ solution to form a soft-gel (FIG. 5a). In contrast, h9e formed a hard hydrogel in acidic conditions, the nanofibers of which aggregated parallel as thicker fibers and entangled as a network (FIG. 5d). Under the observation of an LSCM of the microporous morphology presented in the h9e $Ca^{2+}$ hydrogel (FIG. 5b), the nanofibers crossed one another and aggregated like nanoparticles at the crossing points, while a tangle of more robust fibers was observed in the h9e acidic hydrogel (FIG. 5e). The pores of the h9e hydrogel were bigger and more obvious in $Ca^{2+}$ than in acidic conditions as shown in SEM images (FIGS. 5c and 5f). The circular dichroism (CD) spectra (FIG. 6) suggested that the h9e adopted predominantly β-sheet form in the $Ca^{2+}$ solution, whereas a more random structure was detected in the acidic solution, which has a much lower intensity as well. This suggests disordered chain conformations of the h9e acidic hydrogel.

Figure 7:
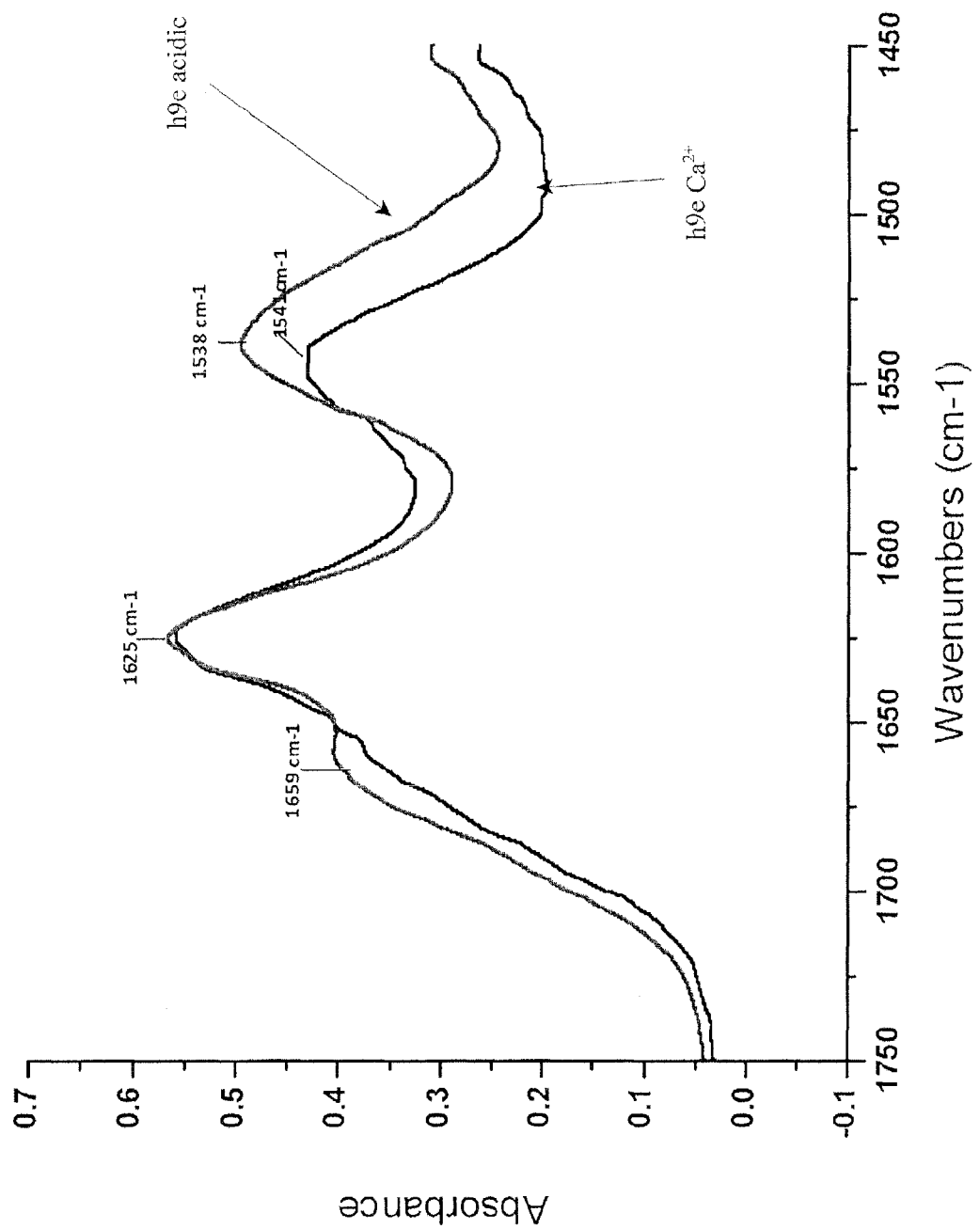
FIG. 7 is a graph showing the FTIR spectra of h9eCa$^{2+}$ and h9e acidic hydrogels.

FIG. 7 shows the amide I and amide II regions of the FTIR spectra of h9e $Ca^{2+}$ and acidic hydrogels. The major amide I peak of both hydrogels appeared at 1625 cm$^{-1}$, indicating that the peptide adopts mainly the β-sheet structure. In addition, some random structures represented by a small peak at 1659 cm$^{-1}$ were observed in the acidic h9e hydrogel. Normally, stable chain conformations are considered as essential factors in the formation and strength of hydrogels, however, the h9e acidic hydrogel, which has even a greater strength than h9e $Ca^{2+}$ hydrogels at concentrations lower than 5 mM (FIG. 4), does not follow this common rule.

Figure 8:
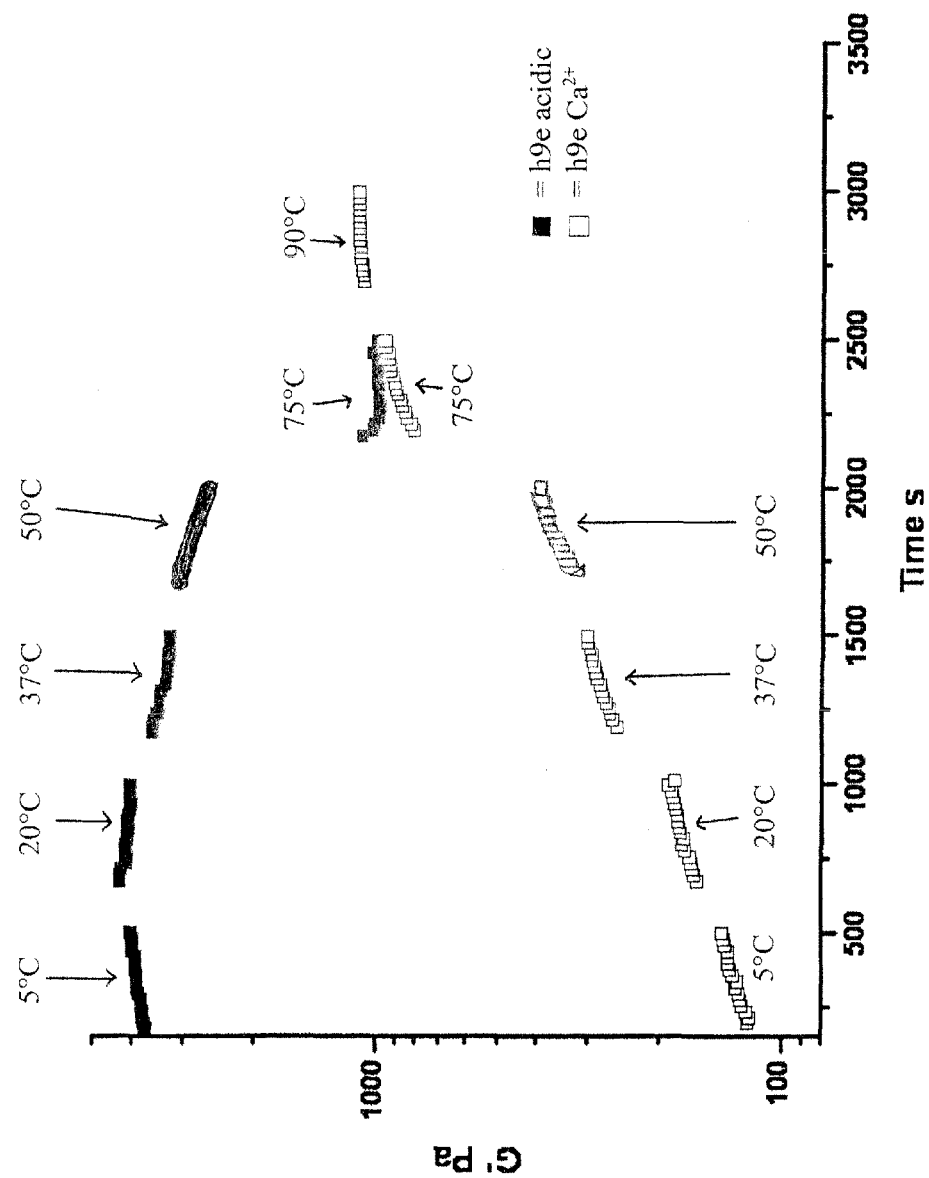
FIG. 8 is a graph showing the temperature profile test of the h9eCa$^{2+}$ (open) and h9e (solid) acidic hydrogels.
Figure 9:
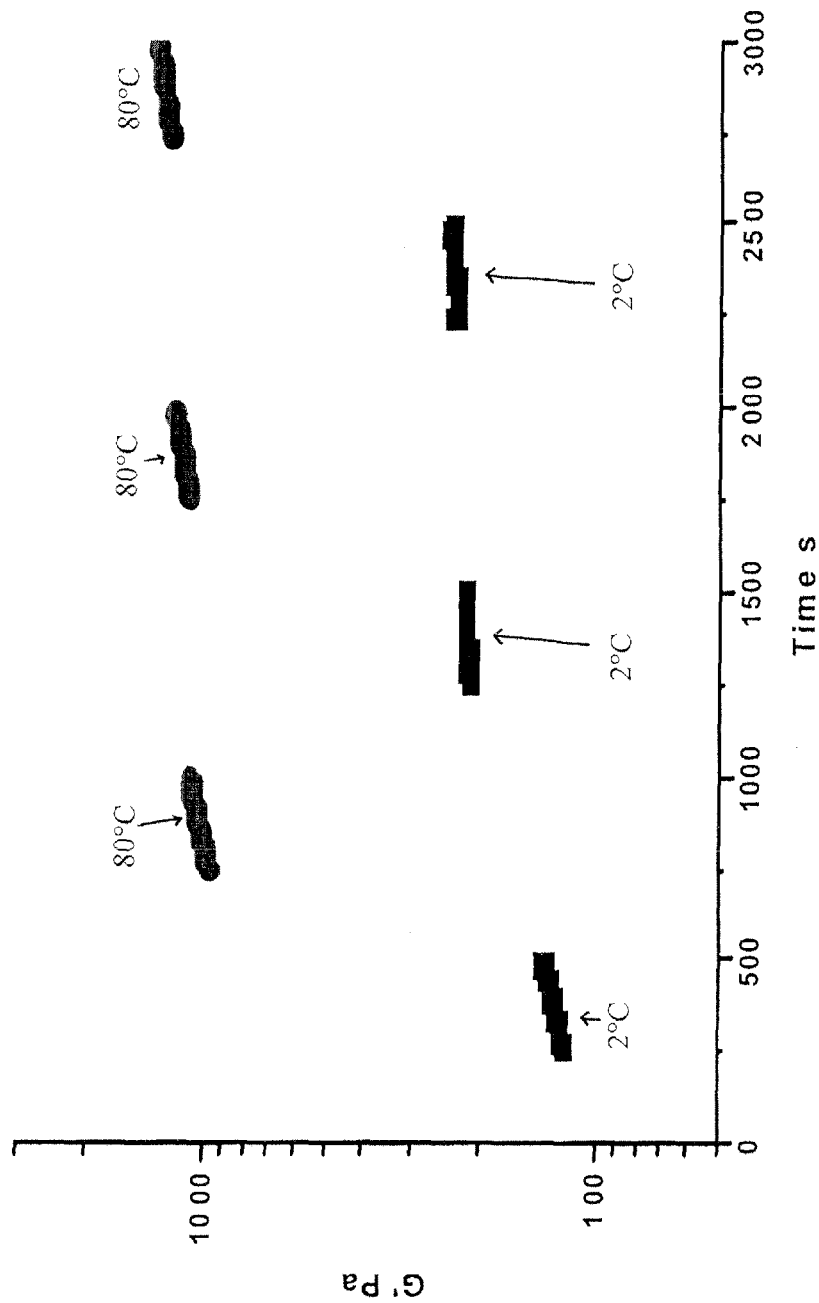
FIG. 9 is a graph depicting the thermal reversibility of G' of h9eCa$^{2+}$ hydrogels.
Figure 10:
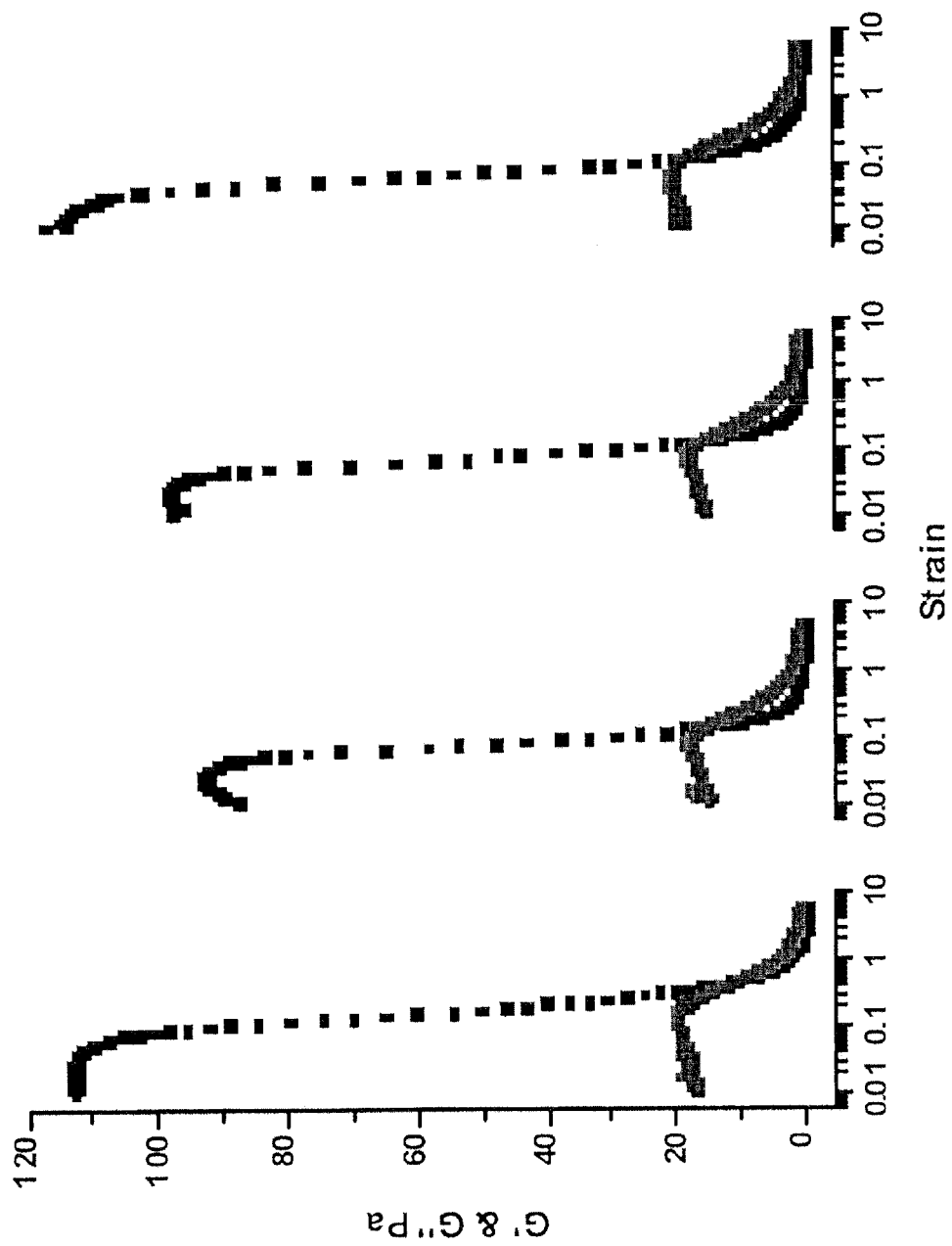
FIG. 10 is a graph depicting the G' (larger peak) and G" (small peak) values of h9eCa$^{2+}$ hydrogels under four sweep shear circles, with the time interval between each cycle being 10 seconds, 30 seconds, and 60 seconds, respectively.

The storage moduli (G') of the h9e acidic gel is about 10 times higher than that of the h9e $Ca^{2+}$ gel at 2.5 mM peptide concentration (FIG. 4). The difference between G' of these two hydrogels became smaller as peptide concentration increased. For example, at 10 mM, G' of the h9e $Ca^{2+}$ gel was about 9,000 Pa, which was even higher than that of the h9e acidic gel (about 8,000 Pa). In a temperature profile test, G' of the h9e $Ca^{2+}$ hydrogel increased 10-fold as the temperature increased from 5 to 90° C., however, G' of the h9e acidic hydrogel decreased as the temperature increased and dropped to 1,000 Pa at 75° C. (FIG. 8). The G' of h9e $Ca^{2+}$ hydrogel was reversible, based on the changing of the temperature within a range of 2 to 80° C. (FIG. 9). The reversibility of the storage moduli with temperature fluctuations was not observed in the h9e acidic hydrogel. The shear thinning and rapid recovery of mechanical strength was found only in the h9e $Ca^{2+}$ hydrogel (FIG. 10).

Figure 11:
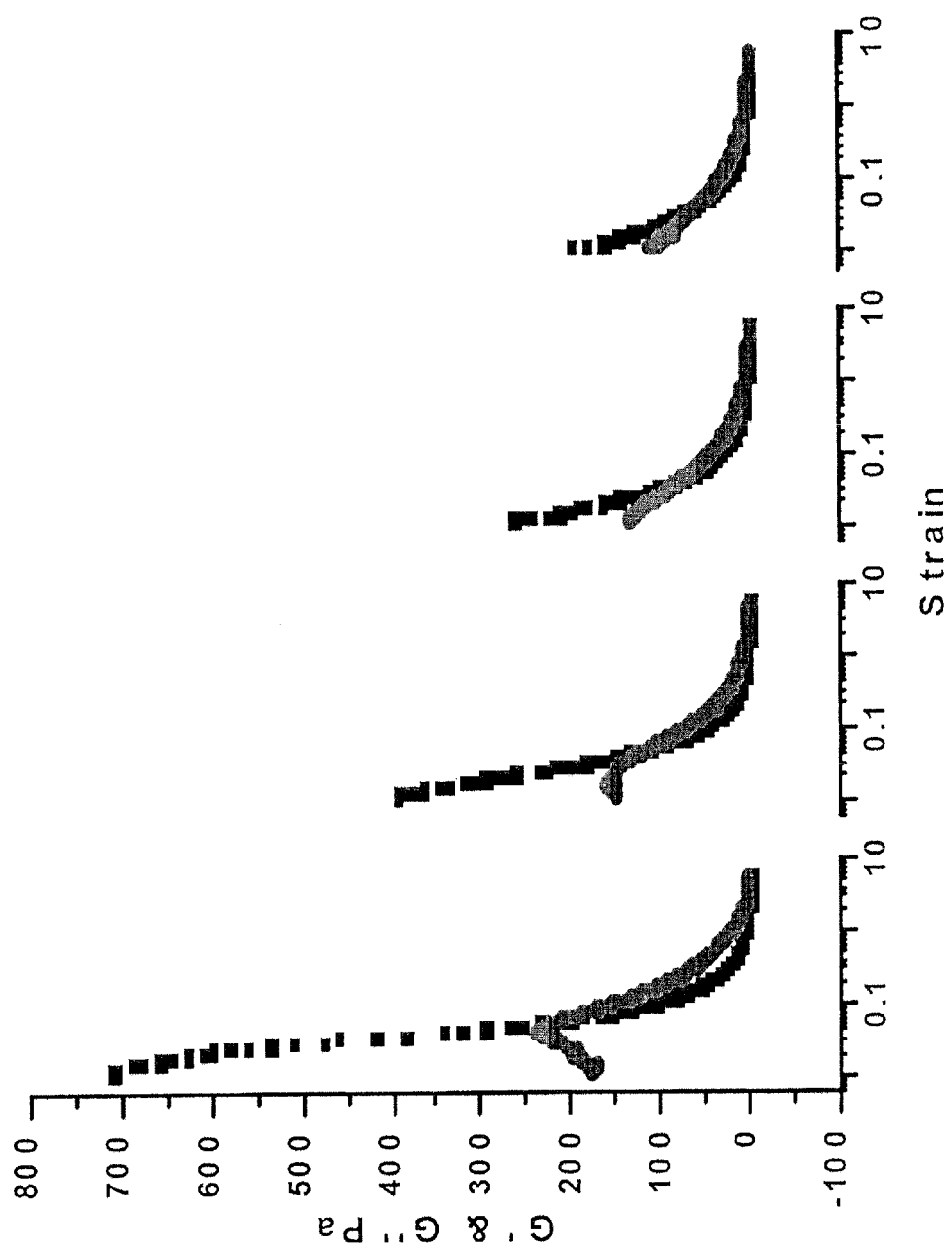
FIG. 11 is a graph depicting the G' (larger peak) and G" (smaller peak) values of h9e acidic hydrogels under four sweep shear circles, with the time interval between each cycle being 10 seconds, 30 seconds, and 60 seconds, respectively.

The hydrogels were also subjected to a serial amplitude sweep test, which tests the shear thinning and recovery properties of the hydrogels. There was a short delay between every two test cycles. The gel appeared to become a pure liquid (G''>G'≈0) under a 500% strain oscillation. After 10 seconds of the first cycle, 75-80% of the hydrogel strength was recovered. The percentage of strength recovery increased as the delay time increased and reached 100% recovery by 60 seconds. Under the same process, the strength of the h9e acidic hydrogel did not recover in this short time period (FIG. 11). The multiple recovery properties and short recovery time suggest that the h9e $Ca^{2+}$ hydrogel has excellent potential for biomedical application.

Figure 12:
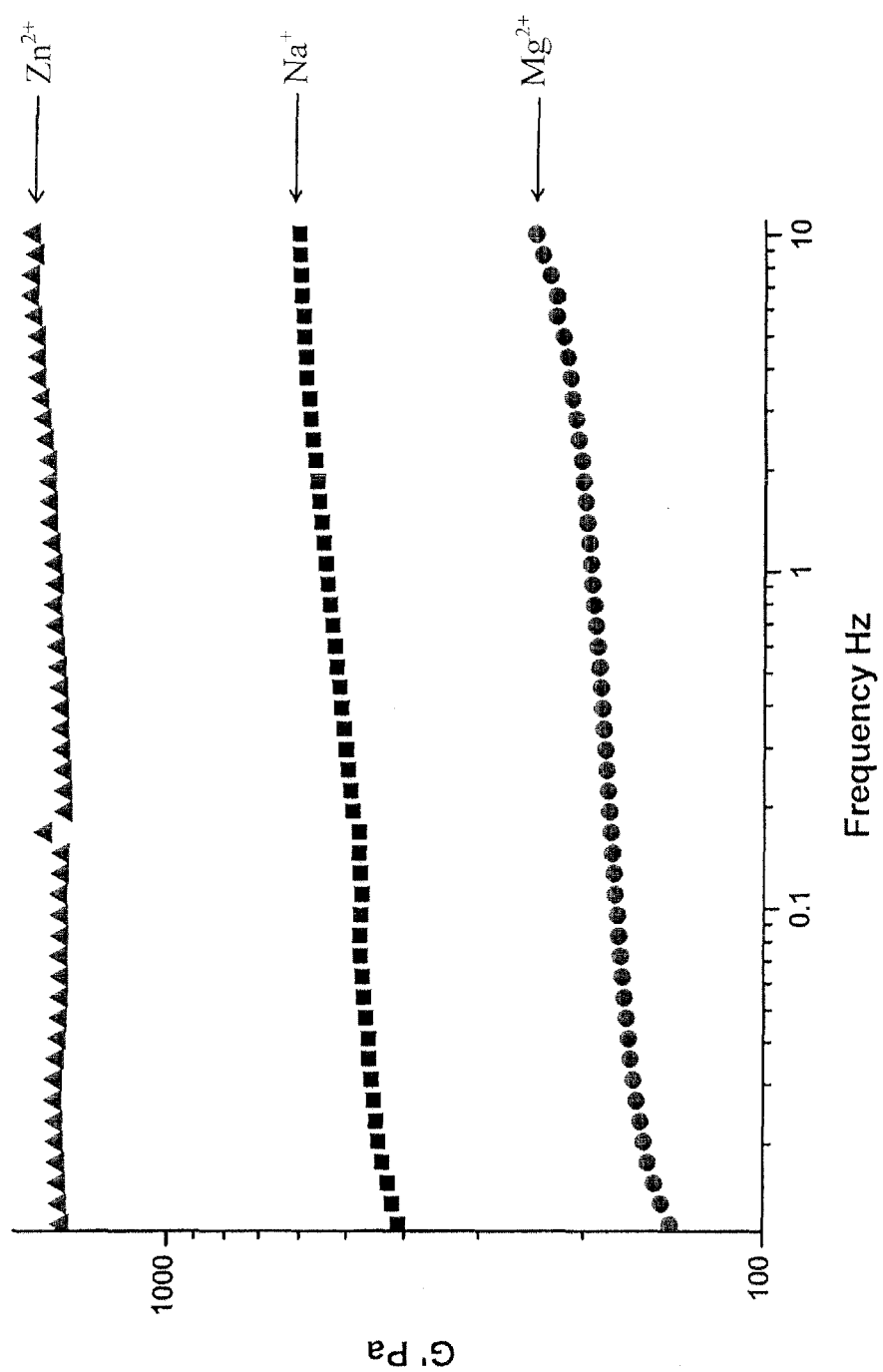
FIG. 12 is a graph showing the G' values of h9e hydrogels formed in Na$^+$, Mg$^{2+}$, and Zn$^{2+}$ solutions at peptide concentrations of 0.005M.
Figure 13:
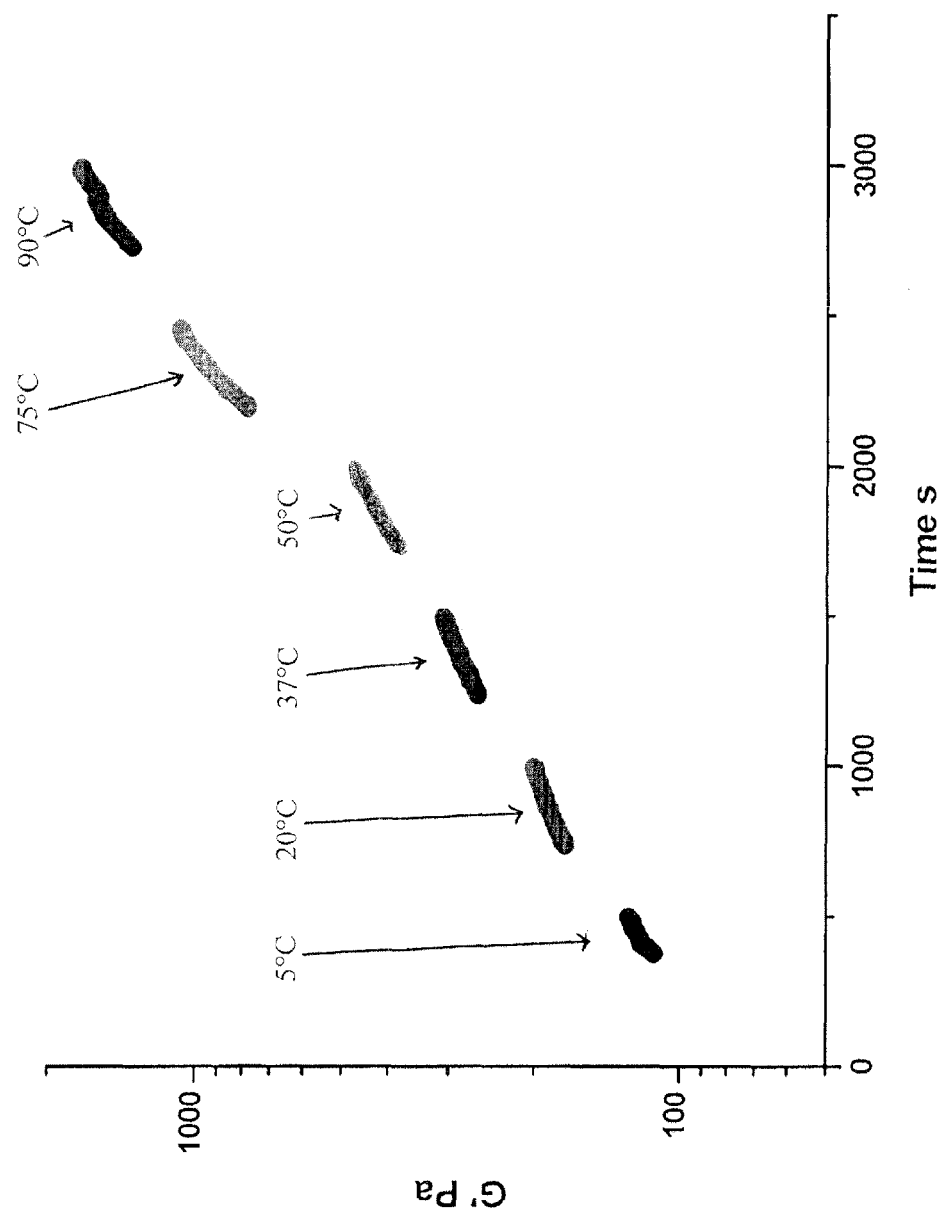
FIG. 13 is a graph depicting the temperature profile test results of an h9eNa$^+$ hydrogel.
Figure 14:
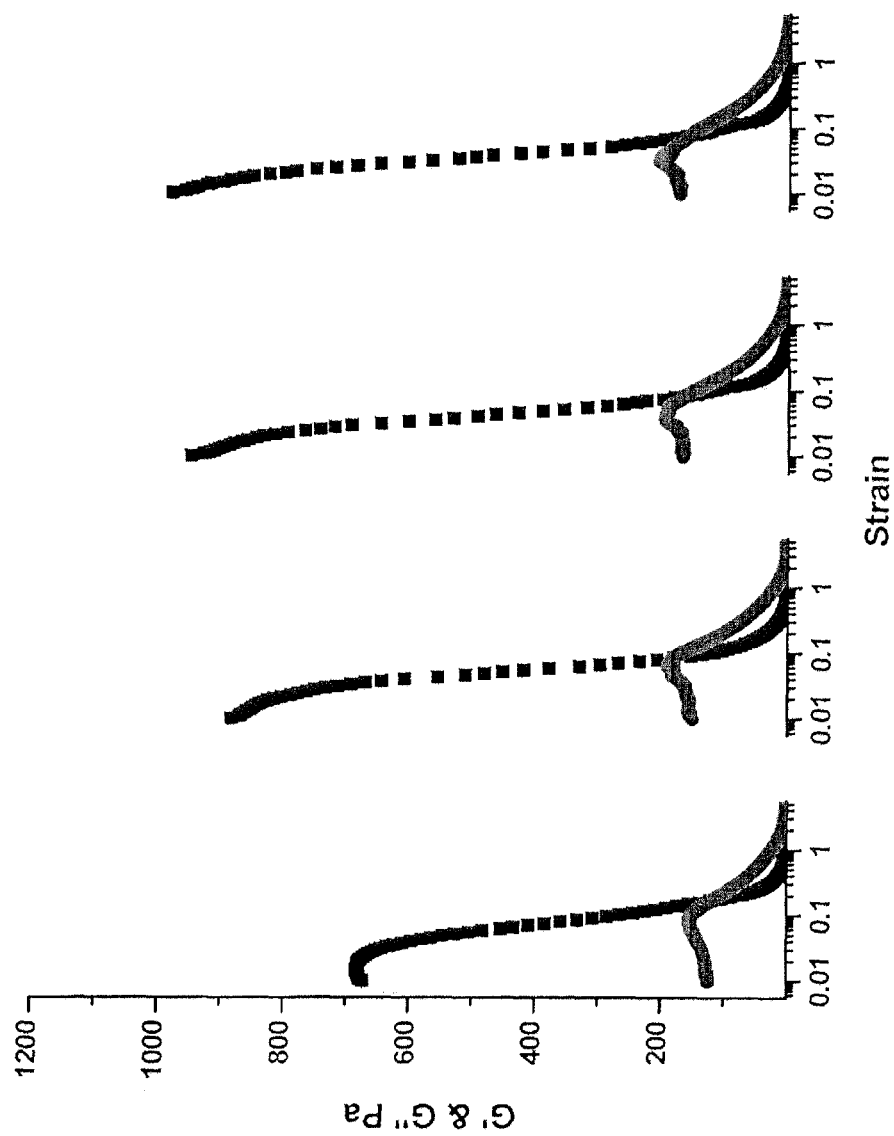
FIG. 14 is a graph depicting the G' (larger peaks) and G" (smaller peaks) values of an h9eNa$^+$ hydrogel under four amplitude sweep shear circles, with the time interval between each cycle being 10 seconds, 10 seconds, and 30 seconds, respectively.
Figure 15:
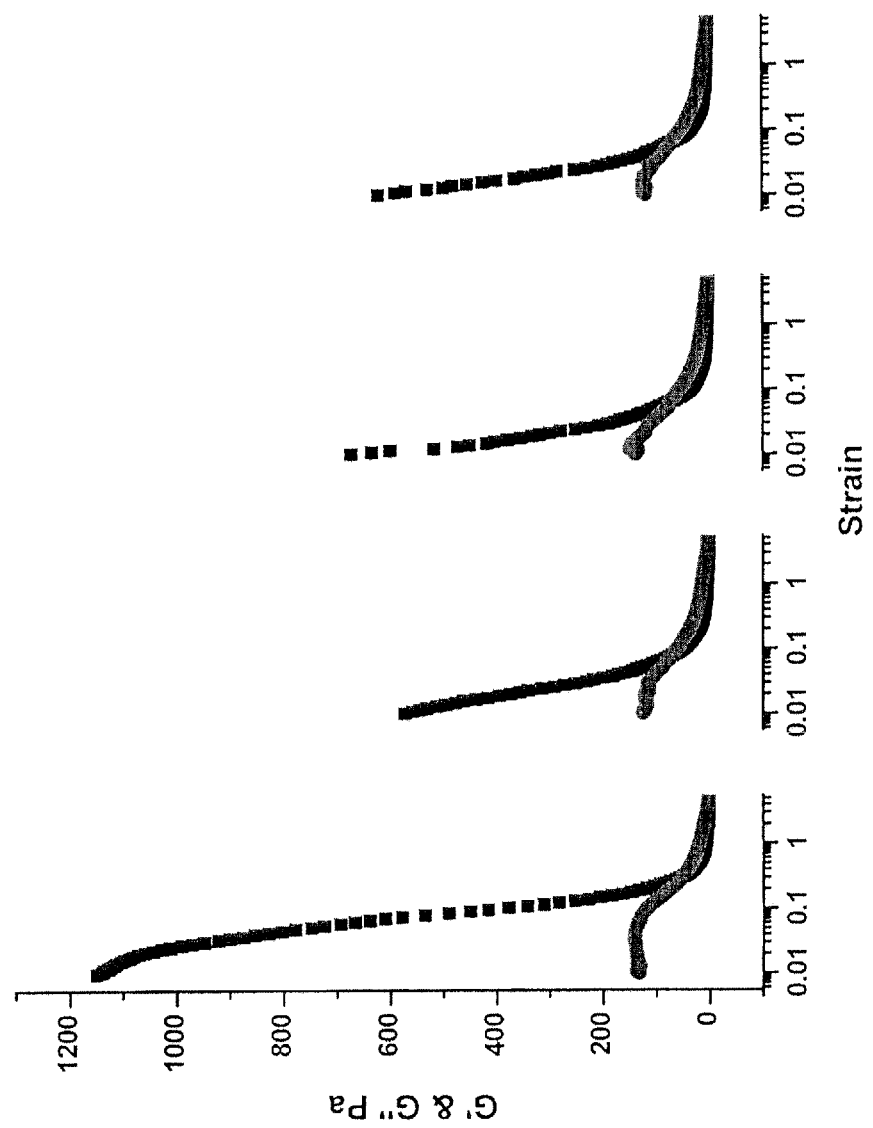
FIG. 15 is a graph displaying the G' (larger peaks) and G" (smaller peaks) values of an h9eMg$^{2+}$ hydrogel under four amplitude sweep shear circles, with the time interval between each cycle being 10 seconds, 1 minute, and 5 minutes, respectively.
Figure 16:
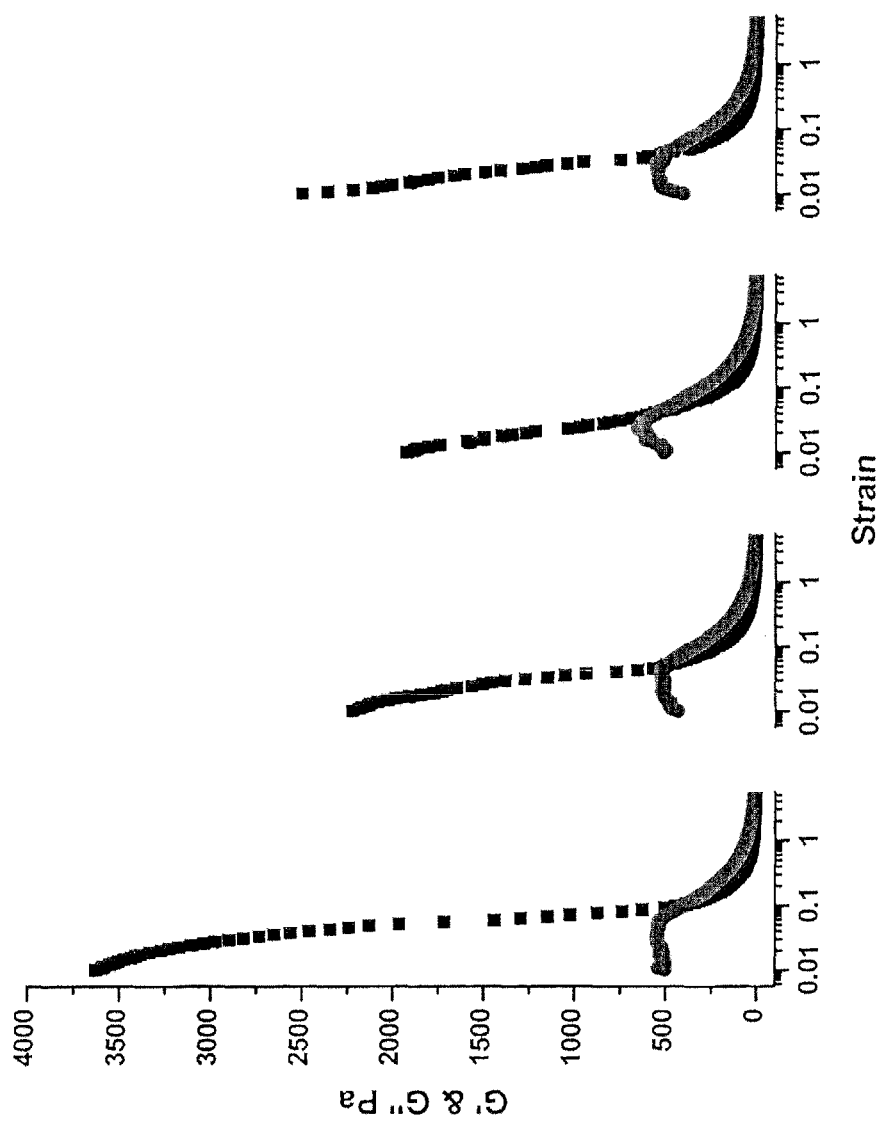
FIG. 16 is a graph displaying the G' (larger peaks) and G" (smaller peaks) values of an h9eZn$^{2+}$ hydrogel under four amplitude sweep shear circles, with the time interval between each cycle being 10 seconds, 1 minute, and 5 minutes, respectively.

Ions of Na$^+$, Mg$^{2+}$, and Zn$^{2+}$ were also studied with h9e. In these three ion solutions, h9e formed hydrogels with a different G' (FIG. 12). The h9e Na$^+$ hydrogel had physical properties similar to those of the h9e $Ca^{2+}$ hydrogel (FIGS. 13 and 14). However, the h9e formed a softer hydrogel in the Mg$^{2+}$ solution. In the Zn$^{2+}$ solution, the h9e formed a hard hydrogel as was the case with the h9e acidic gel. The rapid shear strength recovery property was not found in the h9e Mg$^{2+}$ or h9e Zn$^{2+}$ hydrogels (FIGS. 15 and 16).

We claim:

1. A gel comprising an amphiphilic peptide comprising a hydrophobic terminal region, a turning region, and a hydrophilic terminal region, said turning region being between said hydrophobic and hydrophilic terminal regions, wherein: said hydrophobic region comprises, in any order, amino acid residues of FLIVI (SEQ ID NO:4);

said hydrophilic region is selected from the group consisting of:

[GPGXD]$_n$ (SEQ ID NO: 15), where n is from 1 to 10, and each X is G or A;

GPGX$^1$DGX$^2$X$^1$X$^1$D (SEQ ID NO: 14), where each X$^1$ is individually selected from the group consisting of A, G, V, I, and L, and X$^2$ is selected from the group consisting of P, A, G, V, I, and L; and GPGXD (SEQ ID NO: 16), where X is selected from the group consisting of A, G, V, I, and L; and said turning region is selected from the group consisting of:

G, GG, GGG, GGGG (SEQ ID NO: 17), GSXX (SEQ ID NO: 18), XGSX (SEQ ID NO:19), XXGS (SEQ ID NO:20), SGXX (SEQ ID NO:21), XSGX (SEQ ID NO:22), XXSG (SEQ ID NO:23), GXSX (SEQ ID

NO:24), XGXS (SEQ ID NO:25), SXGX (SEQ ID NO:26), XSXG (SEQ ID NO:27), GXXS (SEQ ID NO:28), SXXG (SEQ ID NO:29), where each X is individually selected from the group consisting of G, I, V, A, and L, and each S could be replaced by T.

2. The gel of claim 1, wherein said turning region consists of amino acid residues GSII (SEQ ID NO:30).

3. The gel of claim 1, wherein said hydrophilic region comprises amino acid residues of GPGGDGPGGD (SEQ ID NO:2).

4. The gel of claim 1, wherein said peptide comprises less than about 30 amino acid residues.

5. The gel of claim 1, wherein said peptide comprises the amino acid sequence FLIVIGSIIGPGGDGPGGD (SEQ ID NO:1).

6. The gel of claim 1, wherein said gel comprises said peptide dispersed, dissolved, or suspended in water.

7. The gel of claim 1, wherein said peptide is present in said gel at a level of from about 0.1% by weight to about 3% by weight, based upon the total weight of the gel taken as 100% by weight.

8. An amphiphilic peptide comprising a turning region, a terminal hydrophobic region and a terminal hydrophilic region, wherein:
said hydrophobic region comprises, in any order, amino acid residues of FLIVI (SEQ ID NO:4);
said hydrophilic region is selected from the group consisting of:
[GPGXD]$_n$ (SEQ ID NO: 15), where n is from 1 to 10, and each X is G or A;
GPGX$^1$DGX$^2$X$^1$X$^1$D (SEQ ID NO: 14), where each X$^1$ is individually selected from the group consisting of A, G, V, I, and L, and X$^2$ is selected from the group consisting of P, A, G, V, I, and L; and
GPGXD (SEQ ID NO: 16), where X is selected from the group consisting of A, G, V, I, and L; and
said turning region is selected from the group consisting of:
G, GG, GGG, GGGG (SEQ ID NO: 17), GSXX (SEQ ID NO: 18), XGSX (SEQ ID NO:19), XXGS (SEQ ID NO:20), SGXX (SEQ ID NO:21), XSGX (SEQ ID NO:22), XXSG (SEQ ID NO:23), GXSX (SEQ ID NO:24), XGXS (SEQ ID NO:25), SXGX (SEQ ID NO:26), XSXG (SEQ ID NO:27), GXXS (SEQ ID NO:28), SXXG (SEQ ID NO:29), where each X is individually selected from the group consisting of G, I, V, A, and L, and each S could be replaced by T.

9. The peptide of claim 8, wherein said peptide comprises less than about 30 amino acid residues.

10. The peptide of claim 8, wherein said peptide comprises the amino acid sequence FLIVIGSIIGPGGDGPGGD (SEQ ID NO:1).

* * * * *